(12) United States Patent
Vaziri

(10) Patent No.: US 10,687,708 B1
(45) Date of Patent: Jun. 23, 2020

(54) METHOD AND APPARATUS FOR A COMPACT AND HIGH RESOLUTION MIND-VIEW COMMUNICATOR

(71) Applicant: Masoud Vaziri, Richardson, TX (US)

(72) Inventor: Masoud Vaziri, Richardson, TX (US)

( * ) Notice: Subject to any disclaimer, the term of this patent is extended or adjusted under 35 U.S.C. 154(b) by 16 days.

(21) Appl. No.: 16/120,326

(22) Filed: Sep. 3, 2018

Related U.S. Application Data

(63) Continuation of application No. 15/400,399, filed on Jan. 6, 2017, now Pat. No. 10,064,552, which is a
(Continued)

(51) Int. Cl.
| | | |
|---|---|---|
| *H04N 7/00* | (2011.01) | |
| *A61B 5/00* | (2006.01) | |
| *A61N 1/36* | (2006.01) | |
| *G09B 19/00* | (2006.01) | |
| *A61B 5/0476* | (2006.01) | |
| *A61B 5/16* | (2006.01) | |

(Continued)

(52) U.S. Cl.
CPC .......... *A61B 5/0022* (2013.01); *A61B 5/0476* (2013.01); *A61B 5/168* (2013.01); *A61N 1/3606* (2013.01); *G06K 9/0061* (2013.01); *G06K 9/00604* (2013.01); *G09B 19/00* (2013.01); *H04N 5/2253* (2013.01); *H04N 5/2256* (2013.01); *H04N 5/775* (2013.01); *H04N 7/22* (2013.01); *H04N 21/2187* (2013.01); *A61B 2560/0242* (2013.01)

(58) Field of Classification Search
CPC ..... A61B 5/0022; A61B 5/0476; A61B 5/168; A61B 2560/0242; A61N 1/3606; G06K 9/00604; G06K 9/0061; G09B 19/00; H04N 5/2253; H04N 5/2256; H04N 5/775; H04N 7/22; H04N 21/2187
See application file for complete search history.

(56) References Cited

U.S. PATENT DOCUMENTS

| 5,859,921 A | 1/1999 | Suzuki |
| 6,307,526 B1 | 10/2001 | Mann |

(Continued)

OTHER PUBLICATIONS

John Bardsley et al.; Blind Iterative Restoration of Images With Spatially-Varying Blur; 9 pages.
(Continued)

*Primary Examiner* — Frank F Huang

(57) ABSTRACT

An embodiment of a mind-view communication apparatus includes a first portable unit and a second portable unit. The first portable unit includes an eyeglass frame, at least one first optical unit disposed on the eyeglass frame for capturing at least one scene image corresponding to a field of view of a user, and at least one second optical unit disposed on the eyeglass frame for capturing at least one eye image corresponding to at least a portion of at least one eye of the user. The second portable unit is in communication with the first portable unit and includes at least one processor configured for receiving the at least one scene image and the at least one eye image, determining a direction within the field of view to which the at least one eye is directed based upon the at least one eye image, and generating a subset of the at least one scene image based on the determined direction.

20 Claims, 26 Drawing Sheets

Related U.S. Application Data continuation of application No. 13/175,421, filed on Jul. 1, 2011, now abandoned, which is a continuation-in-part of application No. 12/794,283, filed on Jun. 4, 2010, now Pat. No. 8,872,910.

(60) Provisional application No. 61/184,232, filed on Jun. 4, 2009, provisional application No. 61/369,618, filed on Jul. 30, 2010, provisional application No. 61/471,397, filed on Apr. 4, 2011, provisional application No. 61/471,376, filed on Apr. 4, 2011.

(51) Int. Cl.
| | | |
|---|---|---|
| *H04N 7/22* | (2006.01) | |
| *H04N 5/225* | (2006.01) | |
| *G06K 9/00* | (2006.01) | |
| *H04N 21/2187* | (2011.01) | |
| *H04N 5/775* | (2006.01) | |

(56) References Cited

U.S. PATENT DOCUMENTS

| | | | | |
|---|---|---|---|---|
| 6,661,495 | B1 * | 12/2003 | Popovich | C09K 19/544 349/1 |
| 7,331,671 | B2 | 2/2008 | Hammoud | |
| 7,697,024 | B2 * | 4/2010 | Currivan | H04N 7/141 348/14.01 |
| 8,159,519 | B2 | 4/2012 | Kurtz et al. | |
| 9,779,311 | B2 | 10/2017 | Lee et al. | |
| 2003/0122930 | A1 | 7/2003 | Schofiled et al. | |
| 2008/0030592 | A1 | 2/2008 | Border et al. | |
| 2010/0053555 | A1 | 3/2010 | Enriquez et al. | |
| 2010/0277619 | A1 | 11/2010 | Scarf | |
| 2011/0064327 | A1 | 3/2011 | Dagher et al. | |
| 2011/0074931 | A1 | 3/2011 | Bilbrey et al. | |
| 2011/0279666 | A1 * | 11/2011 | Strombom | A61B 3/113 348/78 |

OTHER PUBLICATIONS

Sang-Hyuck Lee et al.; Breaking Diffraction Limit of a Small F-Number Compact Camera Using Wavefront Coding; Center for Information Storage Device; Department of Mechanical Engineering, Yonsei University, Shinchondong, Sudaemungu, Seoul 120-749, Korea; Sep. 1, 2008; vol. 16, No. 18; pp. 13569-13578.

Tod R. Lauer; Deconvolution With a Spatially-Variant PSF; National Optical Astronomy Observatory; Tucson, AZ; arXiv:astro-ph/0208247v1; Aug. 12, 2002; 7 pages.

Suk Hwan Lim and Amnon Silverstein; Estimation and Removal of Motion Blur by Capturing Two Images With Different Exposures; HP Laboratories and NVidia Corp.; HPL-2008-170; Oct. 21, 2008; 8 pages.

William T. Freeman et al.; Example-Based Super-Resolution; Mitsubishi Electric Research Labs; Mar./Apr. 2002; IEEE Computer Graphics and Applications; pp. 56-65.

Edward R. Dowskj, Jr. et al.; Extended Depth of Field Through Wave-Front Coding; Apr. 10, 1995; Optical Society of America; vol. 34, No. 11; Applied Optics pp. 1859-1866.

Maria E. Angelopoulou et al,; FPGA-based Real-time Super-Resolution on an Adaptive Image Sensor; Department of Electrical and Electronic Engineering, Imperial College London; 9 pages.

Patrick Vandewalle et al.; A Frequency Domain Approach to Registration of Aliased Images with Application to Super-resolution; Ecole Polytechnique Federal de Lausanne, School of Computer and Communication Sciences; Department of Electrical Engineering and Computer Sciences, University of California; EURASIP Journal on Applied Signal Processing; vol. 2006, Article ID 71459, pp. 1-14.

Barbara Zitova et al.; Image Registration Methods: a Survey; Department of Image Processing; Institute of Information Theory and Automation Academy of Sciences of the Szech Republic; Image and Vision Computing; pp. 977-1000.

Danny Keren et al.; Image Sequence Enhancement Using Sub-pixel Displacements; Department of computer science; The Hebrew University of Jerusalem; 1988 IEEE; pp. 742-746.

Athanasios Papoulis; A New Algorithm in Spectral Analysis and Band-Limited Extrapolation; IEEE Transactions on Circuits and Systems, Sep. 1975; vol. CAS-22, No. 9; pp. 735-742.

W. Thomas Cathey et al.; New Paradigm for Imaging Systems; Optical Society of America; Applied Optics; Oct. 10, 2002; vol. 41, No. 29; pp. 6080-6092.

Oliver Bowen et al.; Real-Time Image Super Resolution Using an FPGA; Department of Electrical and Electronic Engineering; Imperial College London; 2008 IEEE, pp. 89-94.

Kennet Kubala et al.; Reducing Complexity in Computational Imaging Systems; CDM Optics, Inc.; Sep. 8, 2003; vol. 11, No. 18; Optics Express; pp. 2102-2108.

Maria E. Angelopoulou et al.; Robust Real-Time Super-Resolution on FPGA and an Application to Video Enhancement; Imperial College London; ACM Journal Name; Sep. 2008; vol. V, No. N; pp. 1-27.

Eran Gur and Zeev Zalevsky; Single-Image Digital Super-Resolution a Revised Gerchberg-Papoulis Algorithm; IAENG International Journal of Computer Science; Nov. 17, 2007; pp. 1-5.

Lisa Gottesfeld Brown; A Survey of Image Registration Techniques; Department of Computer Science; Columbia University; Jan. 12, 1992; pp. 1-60.

Pravin Bhat et al.; Using Photographs to Enhance Videos of a Static Scene; University of Washington; Microsoft Research; Adobe Systems; University of California; The Eurographics Association 2007; pp. 1-12.

EyeLink User Manual, SR Research Ltd., Copyright 2005-2008, 134 pages.

EyeLink Data Viewer User's Manual, SR Research Ltd., Copyright 2002-2008, 149 pages.

Malcolm et al. Combining topdown processes to guide eye movements during real-world scene search. Journal of Vision, 10(2):4, pg. 1-11 (2010).

Extrema.m, http://www.mathworks.com/matlabcentral/fileexchange/12275-extrema-m-extrema2-m, Sep. 14, 2006.

Guestrin et al. "General Theory of Remote Gaze Estimation Using the Pupil Center and Corneal Reflections", IEEE Trans. Biomedical Eng., vol. 53, No. 6, pp. 1124-1133, Jun. 2006.

\* cited by examiner

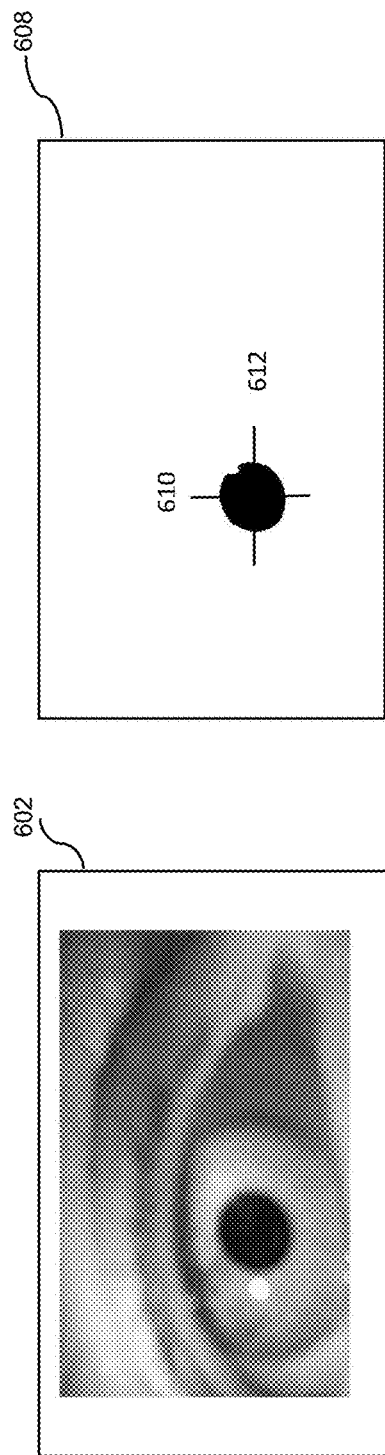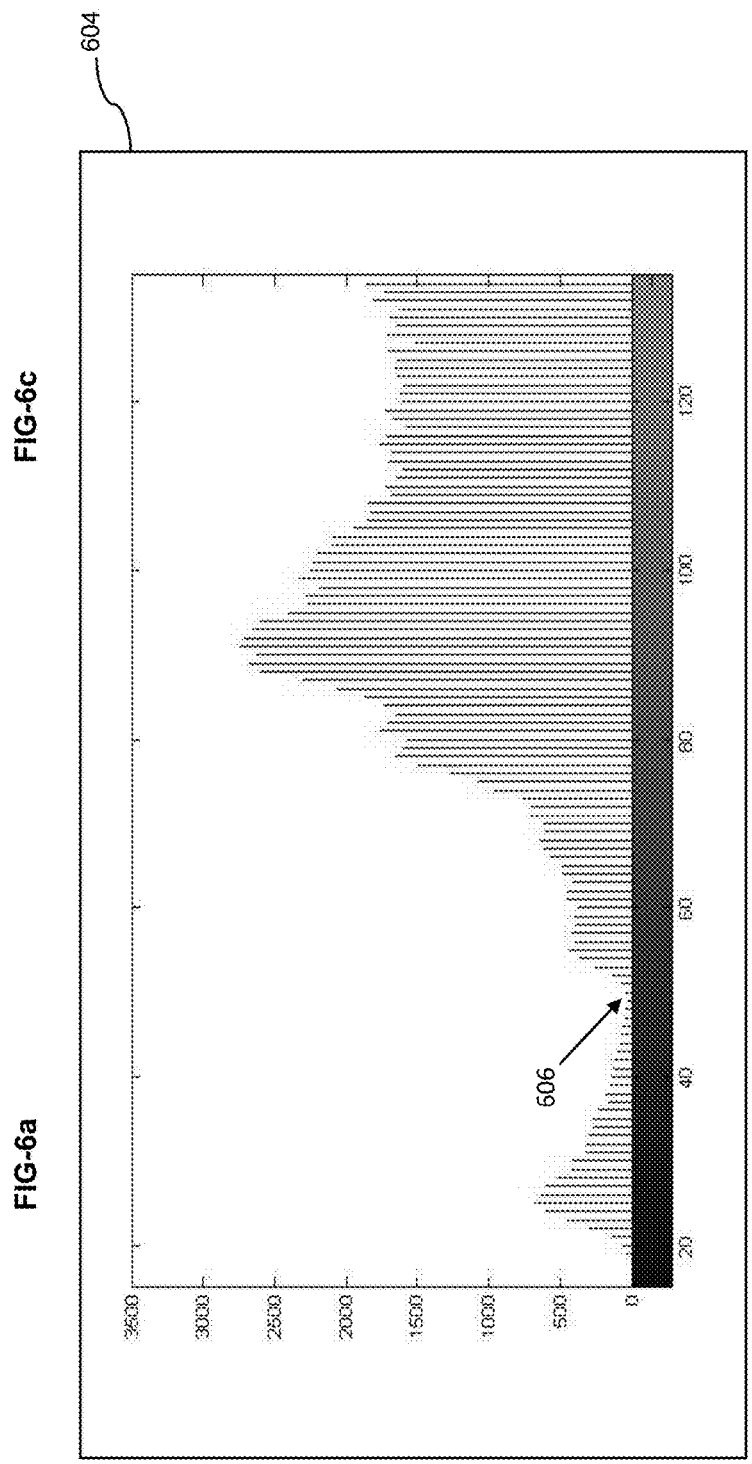
FIG-6a
FIG-6b
FIG-6c

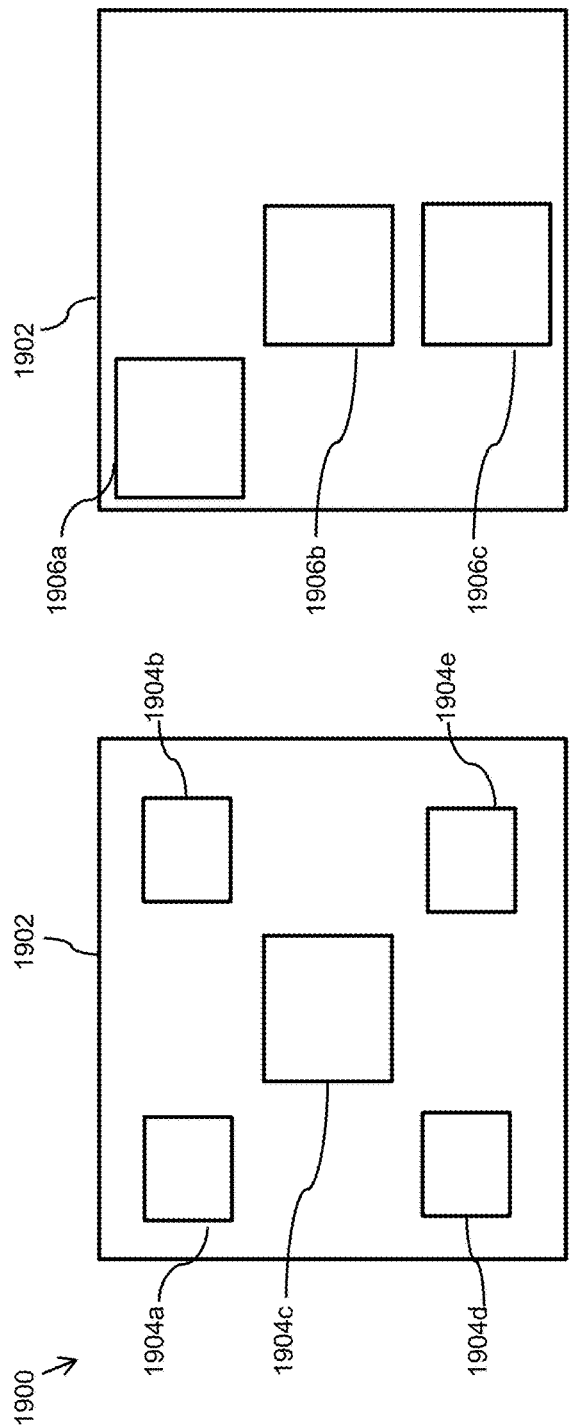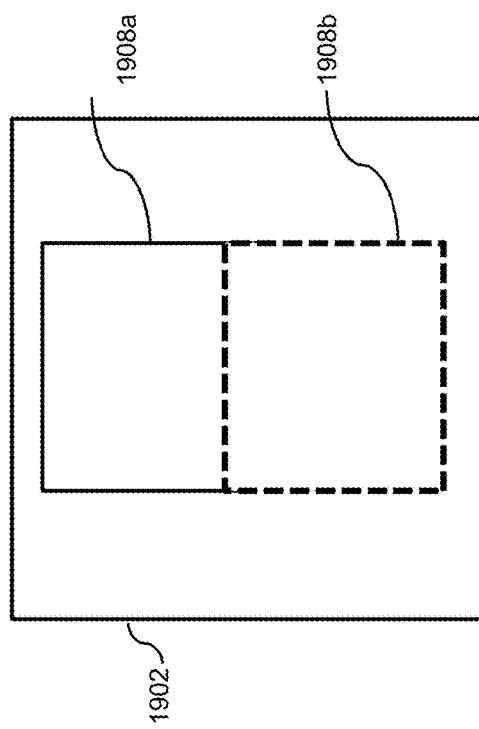

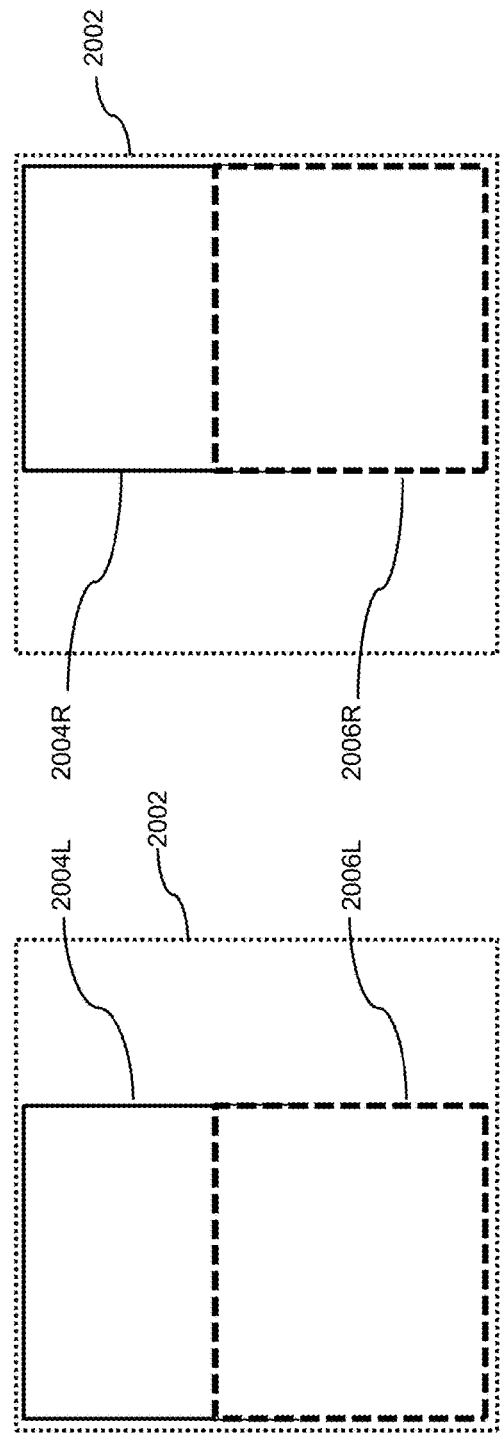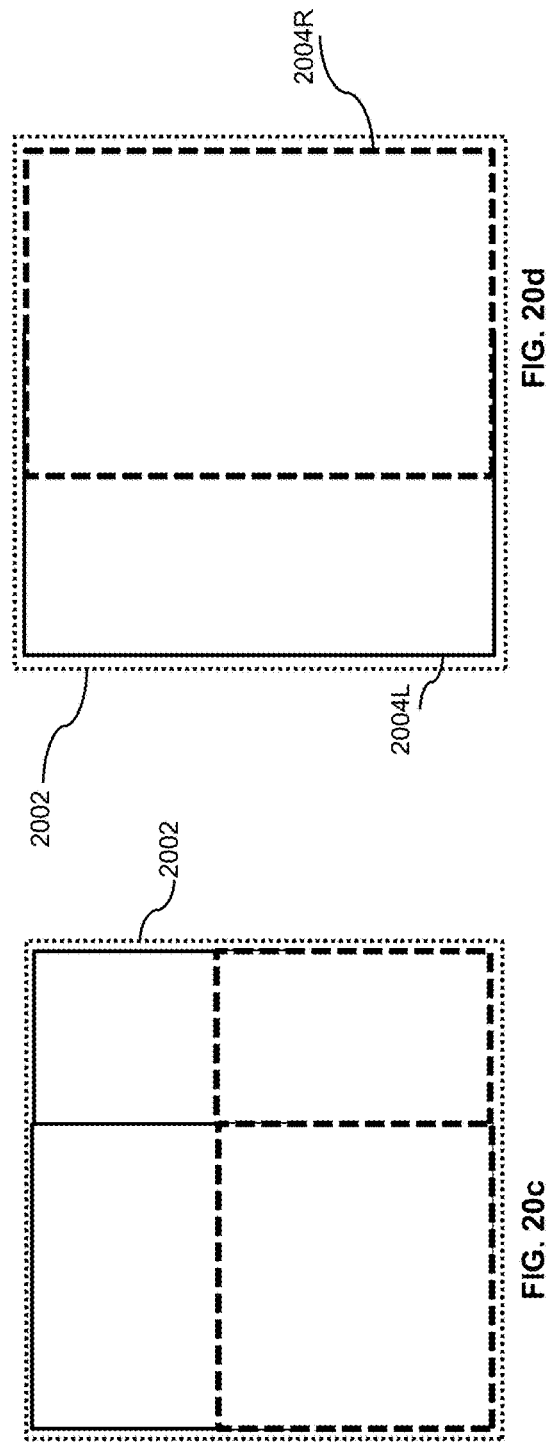

METHOD AND APPARATUS FOR A COMPACT AND HIGH RESOLUTION MIND-VIEW COMMUNICATOR

CROSS-REFERENCE TO RELATED APPLICATIONS

This application is a continuation of U.S. patent application Ser. No. 15/400,399, filed Jan. 6, 2017, and entitled METHOD AND APPARATUS FOR A COMPACT AND HIGH RESOLUTION MIND-VIEW COMMUNICATOR, now U.S. patent Ser. No. 10/064,552 to be issued on Sep. 4, 2014, which is a continuation of U.S. patent application Ser. No. 13/175,421, filed Jul. 1, 2011, and entitled METHOD AND APPARATUS FOR A COMPACT AND HIGH RESOLUTION MIND-VIEW COMMUNICATOR, which is a continuation-in-part of U.S. patent application Ser. No. 12/794,283, filed Jun. 4, 2010, and entitled METHOD AND APPARATUS FOR A COMPACT AND HIGH RESOLUTION EYE-VIEW RECORDER, now U.S. Pat. No. 8,872,910 issued on Oct. 28, 2014, which claims the benefit of U.S. Provisional Application No. 61/184,232, filed Jun. 4, 2009, and entitled METHODS AND APPARATUS FOR A COMPACT AND HIGH RESOLUTION EYE-VIEW RECORDER, all of which are incorporated by reference herein. U.S. patent application Ser. No. 13/175,421 claims the benefits of U.S. Provisional Application No. 61/369,618, filed Jul. 30, 2010, and entitled "Applications for a Compact and High Resolution Eye-View Recorder"; U.S. Provisional Application No. 61/471,397, filed Apr. 4, 2011, and entitled "Eye Tracking Device, Apparatus, and Algorithms"; and U.S. Provisional Application No. 61/369,618, filed Apr. 4, 2011, and entitled "Software-Enabled High Resolution Compact Video Recorder" all of which are incorporated by reference herein.

TECHNICAL FIELD

Embodiments of the invention relate to devices and methods for recording and broadcasting what a user senses. The minimum monitored senses are hearing and vision and the resultant device for these two parameters is a personal video recorder. Pair of eyeglasses frame with integrated opto-electronic devices and a pocket size control unit records the world like a human mind. In essence, this device records short term visual and audio memory in an external device. Autonomous recording of short term memory can be utilized as a medical device for people who suffer from short term memory loss to complement their brain. Live broadcast of such video can be utilized by caregivers of memory patients or by peers on a social network or by real-time collaborators.

BACKGROUND

Cameras and camcorders are two main devices that people use to take pictures and create movies. To use these devices, one uses a viewfinder or display to select a scene or frame. As one is engaged in scene selection, he/she concentrates on what is being recorded. This is fine for professionals whose main job is taking photos or recording movies. However, the majority of camera and camcorder users are individuals who use these devices for personal use. For example, parents videotape their children during birthday parties and other special occasions such as children's performances at schools. As one tries to capture a moment carefully, he/she has to split his attention between recording the event and enjoying the experience. In effect, there is a contradiction between focusing on recording and enjoying the experience fully. Additionally, existing image and video recorder devices cannot be carried around all the time because of their bulk and weight; consequently, many unexpected and one-of-a-kind moments are not recorded. Hence, there is a need for an autonomous device that can record what a user sees, senses and experiences.

SUMMARY

An embodiment of a mind-view communication apparatus includes a first portable unit and a second portable unit. The first portable unit includes an eyeglass frame, at least one first optical unit disposed on the eyeglass frame for capturing at least one scene image corresponding to a subset of the user's total field of view, and at least one second optical unit disposed on the eyeglass frame for capturing at least one eye image corresponding to at least a portion of at least one eye of the user. The second portable unit is in communication with the first portable unit and includes at least one processor configured for receiving the at least one scene image and the at least one eye image, determining a direction within the field of view to which the at least one eye is directed based upon the at least one eye image, and generating a subset of the at least one scene image based on the determined direction.

An embodiment of a method for capturing and processing images includes the steps of capturing at least one scene image corresponding to a field of view of a user by at least one first optical unit disposed on an eyeglass frame, capturing at least one eye image corresponding to at least a portion of at least one eye of the user by at least one second optical unit disposed on the eyeglass frame, receiving the at least one scene image and the at least one eye image by at least one processor, determining a direction within the field of view to which the at least one eye is directed based upon the at least one eye image, and generating a subset of the at least one scene image based on the determined direction.

BRIEF DESCRIPTION OF THE DRAWINGS

For a more complete understanding, reference is now made to the following description taken in conjunction with the accompanying Drawings in which:

FIGS. 6a-6c illustrate steps of acquiring an image, finding an optimum threshold via histogram and a detected pupil;

FIGS. 19a-19c illustrate alternative configurations for high resolution sampling of whole field of view via more than one camera wherein FIGS. 19a, 19b and 19c five, three and two cameras, respectively, are used to sample the FOV of interest;

FIGS. 20a-20c illustrate an embodiment of a four-camera high resolution camera configuration to cover the whole field of view directly in which in FIGS. 20a and 20b the left and right camera modules FOV and their overlap are shown, and in FIG. 20c the net FOV with redundancies are shown;

FIG. 20d illustrates an embodiment of a two high resolution camera solution to cover the entire field of view of interest;

FIGS. 22a-22c depict embodiments of two imaging configurations to shift an image across an image sensor in which FIG. 22a shows a standard configuration for a lens and an imaging device, and FIG. 22b and FIG. 22c illustrate the key additional hardware to achieve image steering;

DETAILED DESCRIPTION

Figure 1:
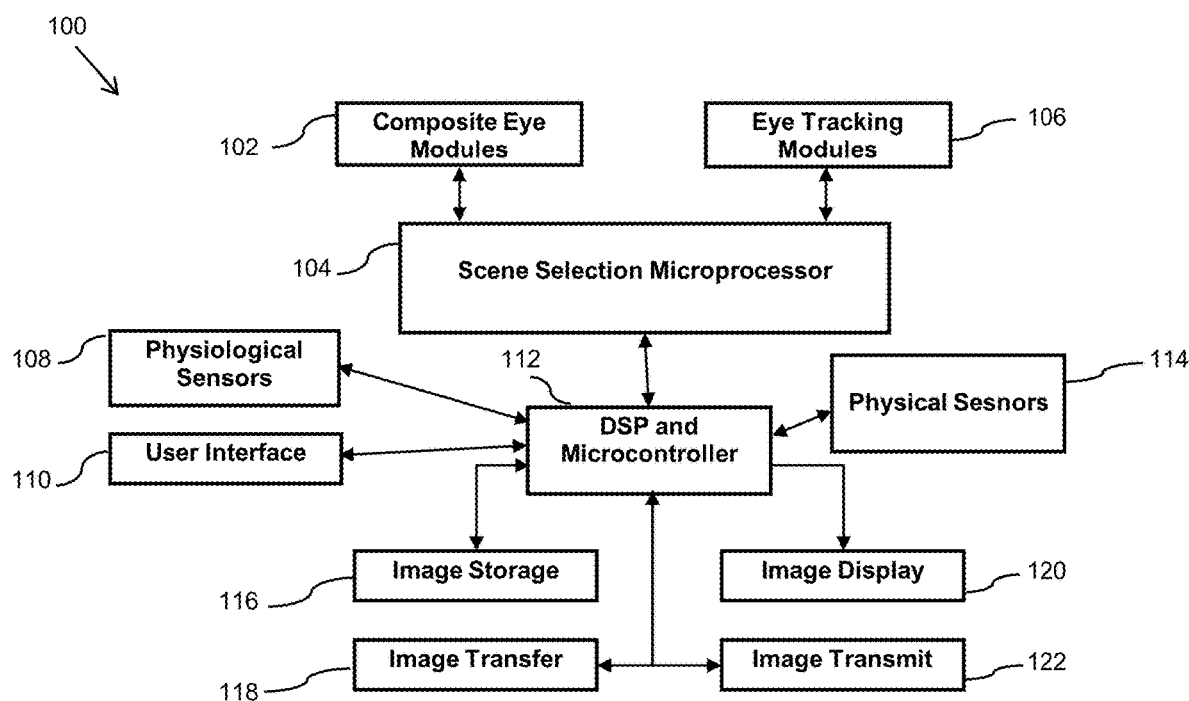
FIG. 1 illustrates simplified block diagrams of an embodiments of the mind-view recorder (MVC)

Referring now to the drawings, wherein like reference numbers are used herein to designate like elements throughout, the various views and embodiments of METHOD AND APPARATUS FOR A COMPACT AND HIGH RESOLUTION MIND-VIEW COMMUNICATOR are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

To address the issue with current cameras and camcorders, embodiments of a wearable and fully automatic video recorder are described herein. As the name "Mind-View Communicator" (MVC) may imply, embodiments of this video recording device view the world like a human eye. It has a similar Field Of View (FOV) and zooming capabilities as those of human eyes.

Various embodiments split the video recording device into two parts: an optical unit that views the world and an electronic box that contains processors, storage, battery, LCD display, user interfaces and communication ports. The optical portion is fitted within an eyeglasses frame and thus becomes wearable. The electronic box can, for example, fit in a pocket or can be worn like a necklace. The box communicates with the frame through either a wired or wireless connection. In a case of wired connection, the user may carry the electronic box, for example, in a pocket. When the box and the frame are connected wirelessly, in various embodiments the eyeglasses frame may be all that is worn by the user.

A feature of various embodiments of the MVC is recording precisely what its user is viewing. To do this, MVC uses eye tracking to follow the user's eyes for scene selection. In this way, the camera records only the frame that the user is looking at. The user can initiate the recording manually by pushing a button on the electronic box or can choose an attention monitoring circuitry to trigger the recording. In the later case, the recording will start automatically as soon as something that interests the user is detected.

In at least one embodiment, the MVC has four distinct building blocks: the Composite Eye (CE), the Eye Tracking (ET), the Sensing Unit (SU) and the Electronic Box (EB). The CE views the world and captures the field of view that is viewable to a pair of human eyes. The ET determines which direction the user's eyes are centered on. A processor on the EB uses the input from the ET and records an image frame that the user's eyes had seen.

Figure 2:
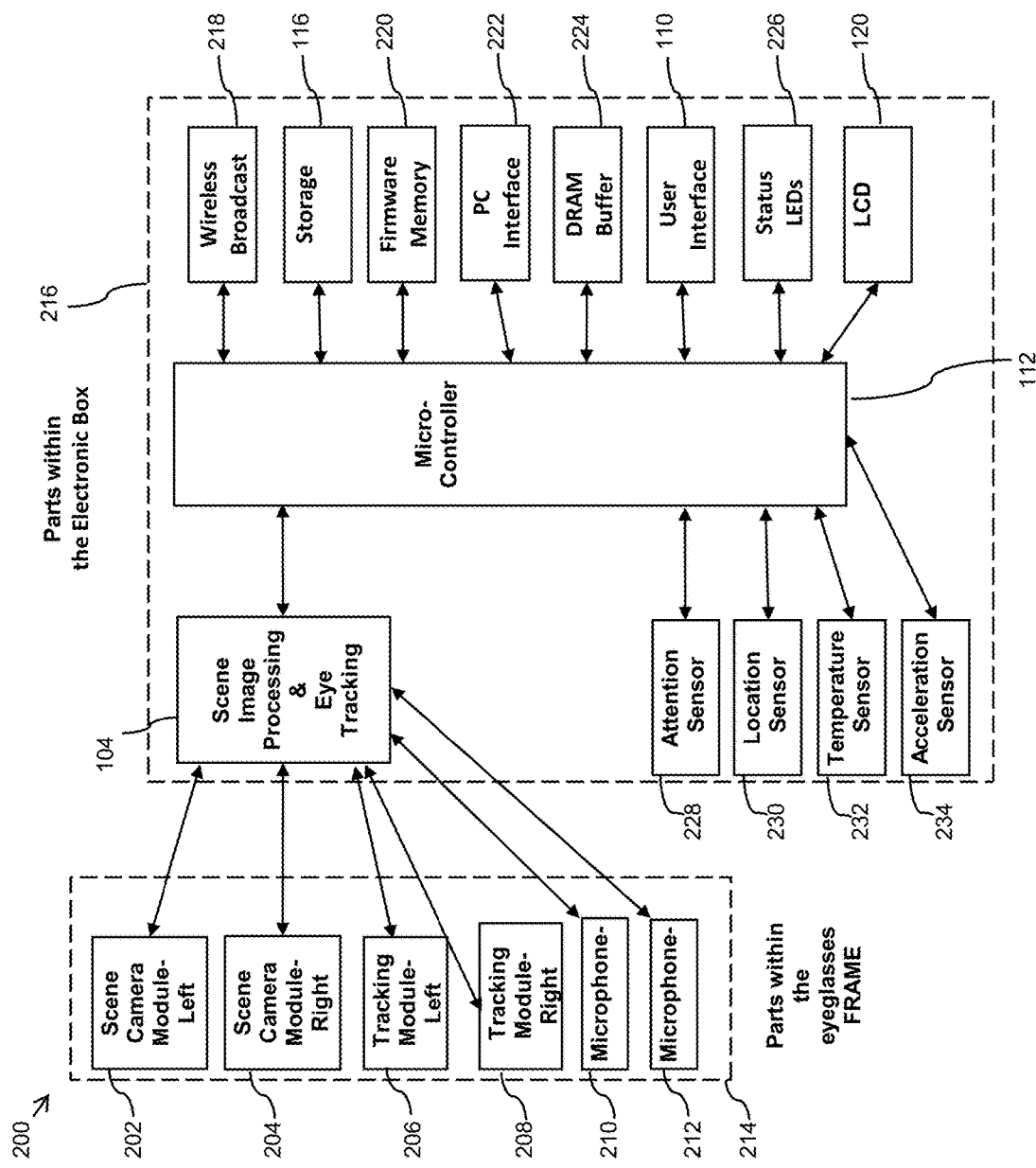
FIG. 2 illustrates simplified block diagrams of another embodiment of the mind-view recorder (MVC)

Simplified block diagrams of embodiments of the MVC are shown in FIG. 1 and FIG. 2. Referring to FIG. 1, the embodiment of the MVC 100 includes Composite Eye Modules 102 in communication with a first Scene Selection Microprocessor module 104, and Eye Tracking Modules 106 in communication also with the Scene Selection Microprocessor module 104. The Scene Selection Microprocessor module 104 is in communication with a DSP and Microprocessor 112. The Physical Sensors 114, Physiological Sensors 108, User Interface module 110, Image Storage module 116, Image Display module 120, Image Transfer module 118, and Image Transmit module 122 are further in communication with the DSP and Microprocessor 112.

The Image Transfer module 118 is an interface such as a USB interface to the DSP and Microprocessor 110, and the Image Transmit module 122 is a wired or wireless interface that has the capability of communicating with an Ethernet port, a wireless device, a wireless access point and/or one or more wireless networks. In at least one embodiment, the Composite Eye Modules 102 and Eye Tracking Modules 106 may utilize serial communication to transfer the image data to the Scene Selection Microprocessor module 104. For example, in a particular embodiment, camera chips based on SMIA (Smart Mobile Interface Architecture) or MIPI (Mobile Industry Processor Interface) providing serial data output may be used. This reduces the number of wires/traces that must run from the frame to the box. Of course, in other embodiments parallel data transfer remains an option if the distance between the frame and the box is reduced significantly. For example, the box can be embedded inside a device attached to head like a headphone.

Referring to FIG. 2, a more detailed embodiment of a MVC 200 includes a frame 214 and a storage/processor box (electronic box) 216 that are connected through wires. The frame includes Scene Camera Module—Left 202, Scene Camera Module—Right 204, Tracking Module—Left 206, Tracking Module—Right 208, and Microphones 210 and 212. The electronic box 216 includes the Scene Selection Microprocessor 104, DSP and Micro-controller 112, Attention Sensor 228, Location Sensor 230, Temperature Sensor 232, Acceleration Sensor 234, Wireless Broadcast module 218, Storage media 116, Memory device for firmware 220, a PC Interface 222, DRAM Buffer 224, User Interface 110, Status LEDs 226, and LCD or touch screen display 120.

In one embodiment, the Composite Eye Modules consists of Scene Camera units 202 and 204 that are in communication with the Scene Selection Microprocessor 104, and the Eye Tracking Modules 206 and 208 are in communication with the Scene Selection Microprocessor 104. The Scene Selection Microprocessor 104, Attention Sensor 228, Location Sensor 230, Temperature Sensor 232, Acceleration Sensor 234, Wireless Broadcast module 218, Storage media 116, Memory device for firmware 220, a PC Interface 222, DRAM Buffer 224, User Interface 110, Status LEDs 226, and LCD or touch screen display 120 are all in communications with the DSP and Micro-controller 112.

The MVC 200 includes right and left scene cameras 202 and 204 which are each coupled to a scene image processor 104. The Scene Selection Microprocessor module 104 is further coupled to a microprocessor 112. The MVC 200 further includes a left eye camera 206 and right eye camera 208 coupled to the Scene Selection Microprocessor module 104. The eye tracking processor 104 is further coupled to the microprocessor 112.

Each of the scene cameras (202 and 204) capture a portion of the field of view of the user of the MVC 200 as image data and provides the image data to the scene image processor 204. The scene image processor 204 then processes the scene image data and provides the processed image data to the microprocessor 112.

The left eye camera 206 provides an image of the left eye of the wearer of the MVC 200 to the Scene Selection Microprocessor module 104 and the right eye camera provides an image of the right eye of the wearer of the MVC 1900 to the Scene Selection Microprocessor module 104. The processor 104 then determines the direction to which each of the eyes of the wearer of the MVC 1900 are directed and provides this information to the microprocessor 112.

An LCD module 120, a storage module 116, and a wireless broadcast module 218 are also in communication with the microprocessor 112. The captured images are then stored in the storage module 116 and may then be viewed in the LCD module 120 and/or wirelessly broadcasted to wireless network using the wireless broadcast module 218.

The MVC 200 further includes status LEDs 226, a PC interface 222, firmware memory 220, a DRAM buffer 224, and a User Interface module 110 also in communication with the microprocessor 112. The status LEDs 226 may provide information about the status of the MVC to the user. The PC interface 222 allows communication of the MVC with a personal computer or other computing device. The firmware memory 220 stores the firmware of the MVC. The User Interface module 110 allows the user to control various aspects and functionalities of the MVC.

The MVC 200 further includes an attention sensor 228, a location sensor 230, a temperature sensor 232, and an acceleration sensor 234 in communication with the microprocessor 112. Each of these sensors may be used to detect an environmental condition or an event and initiate recording of or storing of a captured scene in the Storage Module 116 by the MVC 200 in response to the detected condition or event. For example, the attention sensor 228 may detect whether the user of the MVC is at attention and initiate recording of the current scene if such attention is detected. In a particular embodiment, the attention sensor 228 is a brainwave sensor or measures skin conductivity. The location sensor 230 may detect whether the MVC 200 is at a particular location and initiate recording if such location is detected, or add location information to any recorded video for future search and processing. In a particular embodiment, the location sensor 230 is a GPS sensor. The temperature sensor 232 may detect that a particular temperature has been detected or whether a particular change in temperature has been detected and initiate recording. In at least one embodiment, the acceleration sensor 234 may detect that the MVC 200 has experienced acceleration above a predetermined threshold and then initiate recording of the current scene. In various embodiments, sensor data from one or more sensors may be stored as metadata associated with the recorded video. In a particular embodiment, the microprocessor 112 obtains acceleration data from the acceleration sensor 234 and inserts the acceleration data as metadata associated with the recording video. The metadata may then be used during image search and retrieval of the recorded video. Additionally, the acceleration data may be used during image processing to remove motion blur from some image frames recorded by the MVC 200.

It should be understood that in other embodiments, a sensor used to detect any condition or event may be used to initiate recording or control a particular aspect of the MVC 200. In at least one embodiment, one or more of the attention sensor 228, the location sensor 230, the temperature sensor 232, and the acceleration sensor 234 may be disposed on or within the eyeglasses frame. In still other embodiments, one or more of the attention sensor 228, the location sensor 230, the temperature sensor 232, and the acceleration sensor 234 may be disposed upon or within the electronic box.

In various embodiments the Alpha and Beta brain waves of the user or skin resistivity or other cues such as eye movement patterns are used for monitoring attention. It is well known that when someone starts to pay attention or concentrates, the magnitude of the Alpha waves goes down from its maximum to almost zero while at the same time the intensity of the Beta waves are increased from zero level to a maximum. In a particular embodiment, brainwave detection includes an antenna that is placed within the frame and the temple of the eyeglasses that is used to pick up the Alpha and Beta brain waves of the wearer. The detected brain waves are amplified, filtered out from the noise and provided to the microprocessor 112 within the electronic box. In at least one embodiment, the MVC uses the brainwave detector to automatically start the recording process.

In the embodiment illustrated in FIG. 2, the scene cameras 202 and 204, left eye-camera 206, and right eye camera 208 are disposed within or on the eyeglasses frame and the remaining components are disposed within the electronic box. In still other embodiments, one or more additional components illustrated as being within the electronic box may be disposed on or within the eyeglasses frame.

In at least one embodiment, location and/or date information may be used for tagging captured video and audio information. In various embodiments, a GPS chip is placed on a main board of the electronic box to record location information for various video segments. In some embodiments, time information is also created and recorded along with video.

In various embodiments, various methods may be used for storing video recorded by the scene cameras 202 and 204. In at least one embodiment, on-board memory within the electronic box may be used to store captured video. In other embodiments, a removable memory, such as an SD card, may be interfaced with the electronic box or the eyeglasses frame to record captured video. In still other embodiments, the electronic box communicates wirelessly with one or more networks and the recorded video is stored on one or more network attached storage devices. In various embodiments, the storage device could be a server within a local area network or a server on the Internet.

In various embodiments, the eyeglasses frame and the electronic box communicate with a wired connection and/or a wireless connection. In an embodiment having wired communication, the eyeglasses frame may receive electrical power from the electronic box via one or more wires. In an embodiment having wireless communication, a small battery may be placed within the temples portion of the eyeglasses frame. In both cases, wires may run through the temples for data communication and power delivery. In an embodiment in which the frame is totally passive, no wire goes from the electronic box to the eyeglasses frame. Instead, optical fibers may serve as the communication means between the eyeglasses frame and the electronic box.

In various embodiments, the MVC 200 may use wireless transmission to transmit the images or video captured by the scene cameras 202 and 204 to a server for live broadcast to select users or for further processing. With a live broadcast a user can share his or her experiences with others which may be useful for social networking or real-time collaborations. In still other various embodiments, the MVC 200 can be set to be always on as one mode of operation. In this mode of operation, the MVC 200 uses a user adjustable circular buffer that covers a predetermined time span, for example a one-minute period. With this feature, the user has ample time to capture unexpected moments by initiating storing of the video within the circular buffer.

As described above, in various embodiments the hardware for mind-view recorder may be placed within the eyeglasses frame. This allows installing clear or prescription lenses in the standard lens locations which may be important for many people who use corrective lenses.

In various embodiments the Scene Selection Microprocessor module 104 has a power supply and the associated circuitry on its board. For this configuration, in at least one embodiment it is possible to use a smart phone as the remote storage/processor box 104 as various smart phones already have location sensor, Bluetooth, User Interface, DSP/Microprocessor and access to a wireless network and the Internet. In some embodiments, one or more microphones disposed on the eyeglasses frame 214 can be used for hand-free calling as well. This enables smart phones to record digital still images and videos hands-free. A smart phone can also be used as the electronic box in FIGS. 1 and 2 provided some modifications are made to the smart phone to accept and control the electronics that are installed within the eyeglasses frame. In a particular embodiment, the electronic box is a smart phone with new capabilities and the frame is a hands-free video/audio input gathering device.

Composite Eyes (CE)

To view the world, human eyes can rotate in two directions: up/down and left/right. The eyes can also zoom, even though a limited amount. Duplicating this capability within an eyeglasses frame is not easy considering constraints such as rotation and tilt speed of the lens, the required hardware and its power consumption. Rather than using a single lens that can be tilted in two orthogonal axes, various embodiments use an array of fixed lenses in the viewing optics to cover all the angles that an eye covers for a fixed direction of head movement. This eliminates the need to rotate or tilt a viewing lens. Also smaller lenses are less expensive and cause less distortions. In fact, in various embodiments the array of fixed lenses collects all the information all the time and because of this feature the eye can be tracked in real time. As indicated, the MVC can capture all the details that the user might have or might not have paid attention to. This gives the user a "second" chance to review the visual images that he/she was exposed to. In at least one embodiment, the MVC has three display modes: 1. Show what eyes see (gazing view); 2. Show gaze view and peripheral view; and 3. Interactively display a portion of the total field but chosen by a second user. The third display option is useful for remote collaborations or interactions. For example, a nurse might be examining a patient in a remote area and a doctor in another location can choose what to focus on with higher resolution for objects that are within the FOV of the nurse. In effect, the eye movements of the doctor chooses scene of interest for him/her. This will be an enabler for telemedicine.

Fixed-lens cameras are converging systems and as a consequence, the image size of an object on the detector (camera's retina) becomes smaller as the object moves away from the camera. In human eyes and most cameras the focal length of the system is changed to get a better view of the object. It is possible to extract the object distance from stereo imaging of the scene or from tracking the two eyes. Knowing the distance, the image size can be adjusted similar a human eye. At least some embodiments limit the MVC to duplicating the human eye zoom range and the frame size of the video that it captures is similar to the frame images that a human brain receives. Seeing like a human eye makes embodiments of the device suitable to serve as a memory aid for many people, especially those with memory disorders. In fact such video recordings provide subjective visual perception of the user's environment for the first time.

Optical Modules within the Frame

Figure 3A:
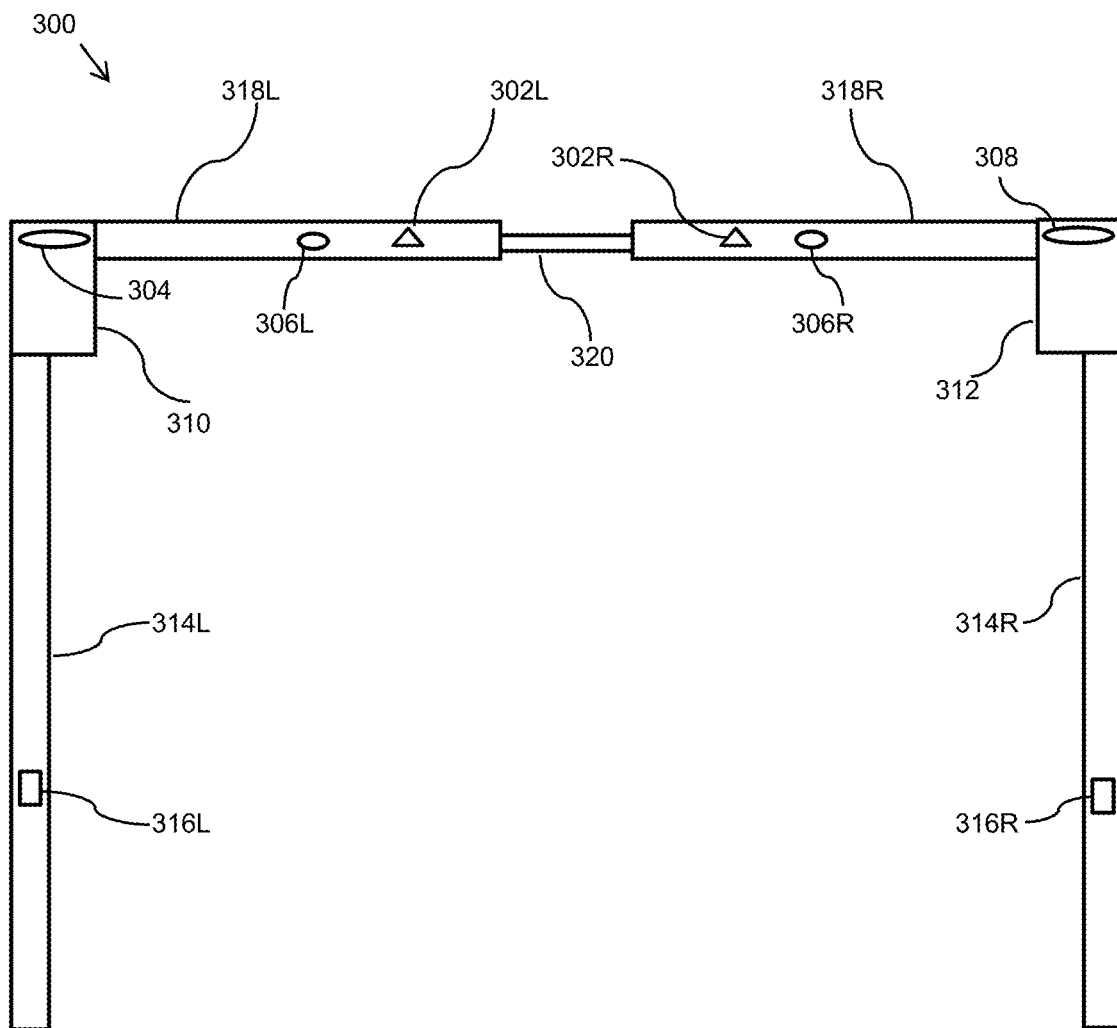
FIG. 3a illustrates a diagram of an embodiment of an MVC frame.
Figure 3B:
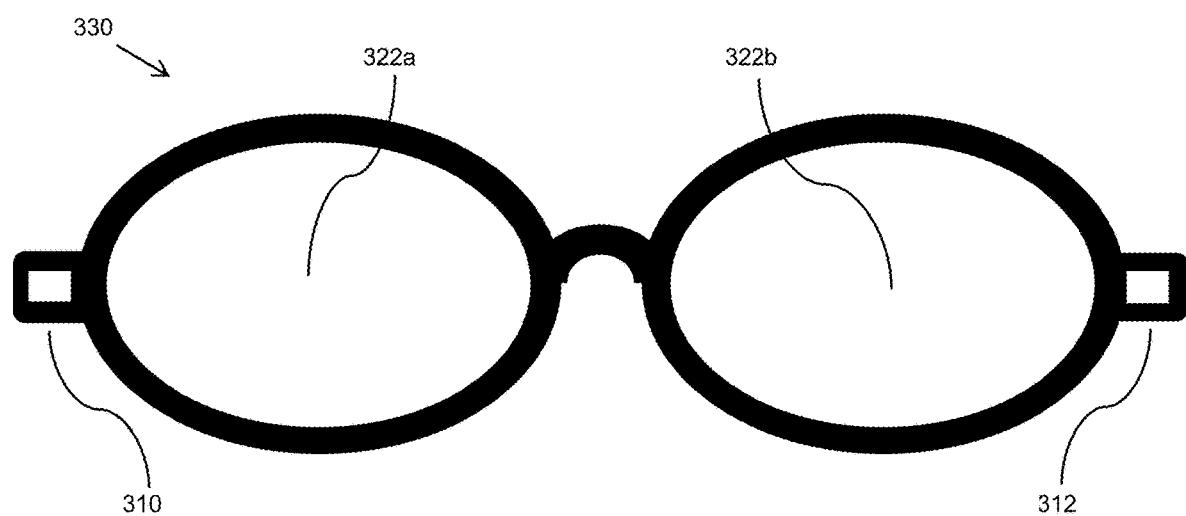
FIGS. 3b and 3c illustrate embodiments of cameras and infra-red LED configurations for the MVC.
Figure 3C:
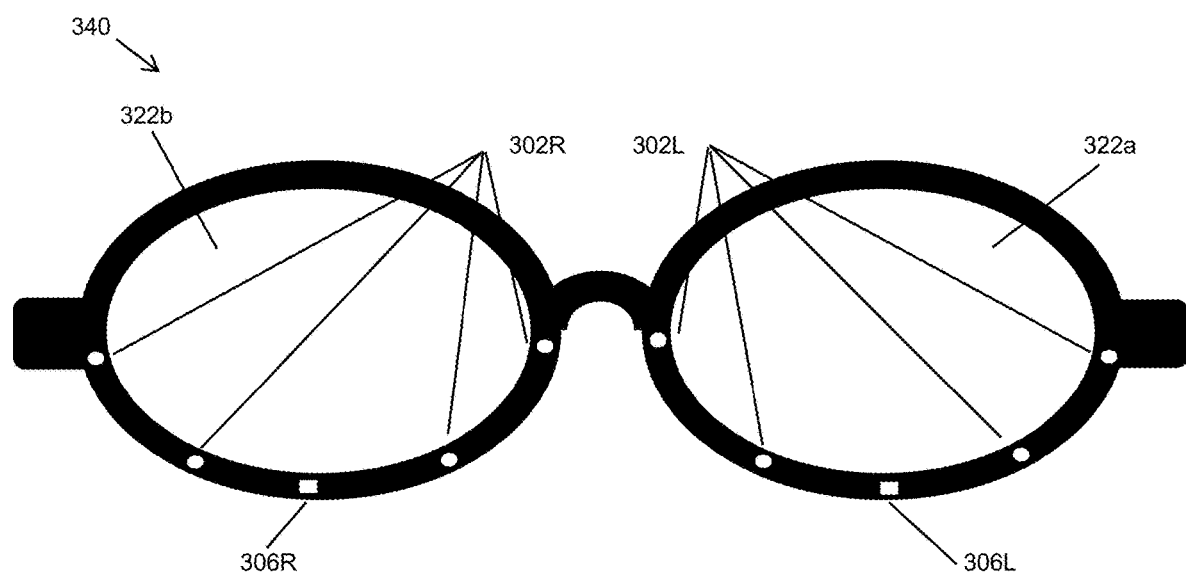

FIGS. 3a-3c illustrate an embodiment of the eyeglasses frame for the MVC and the locations of various modules with respect to each other. FIG. 3a shows an embodiment of the MVC frame 300 consisting of the IR-LED 302, Eye Tracking Cameras 306, Viewing Lenses 304 and 308, Lens Holder area 318, Eyeglasses Bridge 320, Left and Right Camera Modules 310 and 312, Microphones 316, and Temples 314. In the embodiment illustrated in FIG. 3a, the two Right and Left Camera Modules 310 and 312 form the composite eye optics 102 of the MVC, and the Tracking Cameras 306 and IR-LED 302 form the Eye Tracking Modules 106.

An MVC has two groups of cameras or lenses. The embodiment illustrated in FIG. 3a shows an eyeglass frame having a left template 314L (or left arm) coupled to a left eyeglass lens holder area 318L, and a right template 314R (or right arm) coupled to a right eyeglass lens holder area 318R. The left eyeglass lens holder area 318L is coupled to the right eyeglass lens holder area 318R via an eyeglass bridge 320. Scene Cameras can record all or a subset of the user's peripheral view. Tracking Cameras monitor the eyes of the user. In the particular embodiment illustrated in FIG. 3a, a left camera module 306L is disposed within 318L proximate to the left eyeglass lens holder area 318L and a right camera module 306R is disposed within or on the right eyeglass template 318R proximate to the right eyeglass lens holder area 318R. A left tracking lens 306L is disposed in or on the left eyeglass lens holder area 318L proximate to the left camera module 310, and a right tracking lens 306R is disposed in or on the right eyeglass lens holder area 318R proximate to the right camera module 312. The left camera module 310 and the right camera module 312 further include a left viewing lens 304 and a right viewing lens 308, respectively. Note that the infra-red illuminating LEDs that illuminate the eyes surfaces in one or more embodiments are marked as 302 in FIG. 3a.

FIGS. 3b and 3c illustrate embodiments of cameras and infra-red LED configurations for the MVC. FIG. 3b illustrates the front-view of an embodiment of the frame and the embedded Scene Camera Modules 310 and 312. FIG. 3c illustrates the back-view of the frame where the IR-LEDs 302 and tracking cameras 306 are visible. The IR-LEDs 302 illuminate the eye surface and the eye tracking camera pairs 306 point towards users' eyes for taking images of the eyes. The captured images, which in the preferred embodiment are in black and white, are used to map out the location of the center of the eye pupil of each eye. It is well known that the eye pupil absorbs much more infrared light than the tissues around it. This makes the pupil the darkest object in captured images. In a particular embodiment, the detectors used for eye tracking have a resolution of 320×240 or less, and the collecting lens may be a pinhole lens with visible light filter that transmits infrared and blocks visible light. The image gathering lens of the said eye tracking camera may intentionally be set slightly out of focus (defocused) to average over small features in the image of the eye in order to blur out the small features. In such an embodiment, the intentional defocus speeds up the search for a pupil within the frame.

In the embodiment illustrated in FIG. 3c, the eye monitoring lenses or cameras 306 are embedded in the eyeglasses frame 340 below the right and left lenses 322a & 322b, respectively. The left lens 322a has four infrared LEDs or lensed fibers 302L mounted in or on the circumference of the left lens 322a on the eyeglasses frame 340. The right lens 322b has four infrared LEDs or lensed fibers 302R mounted in or on the circumference of the right lens 322b on the eyeglasses frame 340.

In various embodiments, the sources of the illumination light are Infrared LEDs. The IR-LEDs can be placed in the inner side of the eyeglasses frame 340 or be housed in the main electronic box 104. In the later case, lensed optical fibers are used to bring the light to the frame area 214. Lensed optical imaging fibers can also be used to transmit the viewed images of the eye to the electronic box 104 for processing of the eye tracking data. In a particular embodiment an infra-red filter may be used to block the visible ambient light and pass through the light from the IR-LEDs.

In various embodiments, all of the elements that are needed in the electronic box are found or can be easily added to smart phones. Hence, in various embodiments it may be preferable to use such a smart phone as the electronic box 104 because almost everyone is or will be carrying a smart phone. In still other embodiments, phone capability may be added to the electronic box 104. Permanent prescription or sunglasses lenses can also be installed in the MVC frame 214, as shown in FIG. 3c.

As it is desired to increase the FOV and at the same time keep resolution of the captured images, there is a need to increase the number of monitored pixels per second. This effectively means a bigger pipe is needed to transmit the recorded pixel values from the eyeglasses frame to the electronics box. Using wires make the eyeglasses frame heavier. To address this issue, in at least one embodiment optical fibers are used to send the signal outputs down to the electronic box.

Figure 4A:
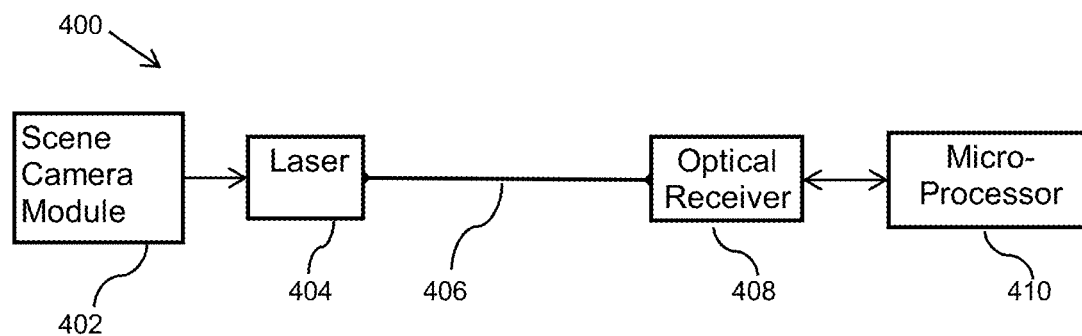
FIG. 4a illustrates a schematic diagram of an embodiment in which camera outputs are transmitted from the eyeglasses frame to the electronic box via a fiber.

FIG. 4a illustrates a schematic diagram of an embodiment in which camera outputs are transmitted from the eyeglasses frame to the electronic box via a fiber Data from Scene Camera Module 402 is received by the Laser module 404 and is converted from an electrical signal into an optical signal. The modulated laser light 404 is coupled into the optical fiber 406 to transmit the light from the frame to the processor 410 in the electronic box. In a particular embodiment, the transmitter source (laser module 404) is a VCSEL (Vertically Coupled Surface Emitting Laser). Such components are extremely small in size, consume low power and have very high reliability rates. In addition, a driver may be integrated with the source to further reduce the space and power consumption. State of art power consumption for a driver and a VSCEL at 10 GB/s is about 15 mW. A metal coated fiber may be used for electrical power deliver to the frame.

Figure 4B:
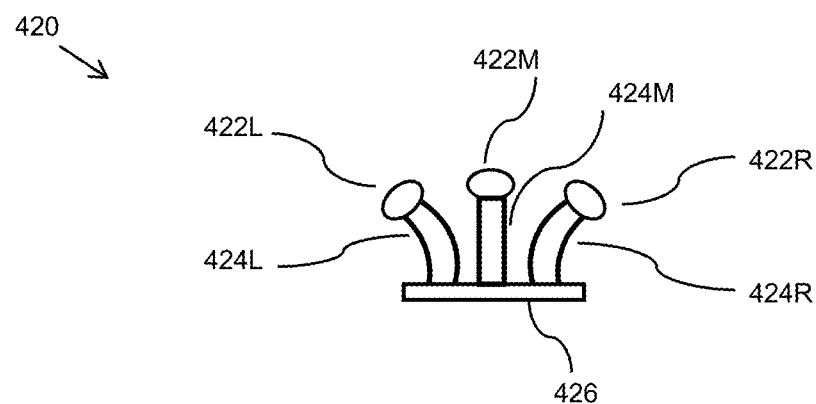
FIG. 4b illustrates the use of tapered fused imaging fibers to couple lights from more than one imaging lens to a single imaging sensor.

In FIG. 4b, an embodiment 420 is illustrated in which fused fiber tapers 424L, 424M and 424R are utilized to couple lenses outputs of lenses 422L, 422M and 422R into a common CMOS detector 426. As an example, the fused fiber tapers by Schott can achieve 100 LP/mm of resolution. An advantage of using a single detector is reducing the electronics in the eyeglasses arms. By using a larger detector, the same Analog to Digital Convertor (ADC) can be used as well as the same image processing unit and reference clock. Consequently, a reduction in power consumption may be achieved compared to the case of in which multiple detectors are used.

Eye Tracking Algorithms and Procedures

A number of techniques have been described for eye tracking such as those described in U.S. Pat. Nos. 5,481,622; 7,736,000; 5,231,674; 5,956,125; 7,633,527; 5,892,566; 7,682,026; 7,391,887; 7,391,887; 7,259,785; and 7,697,032, all incorporated herein by reference. In all these techniques, an image processing technique is employed.

Figure 5:
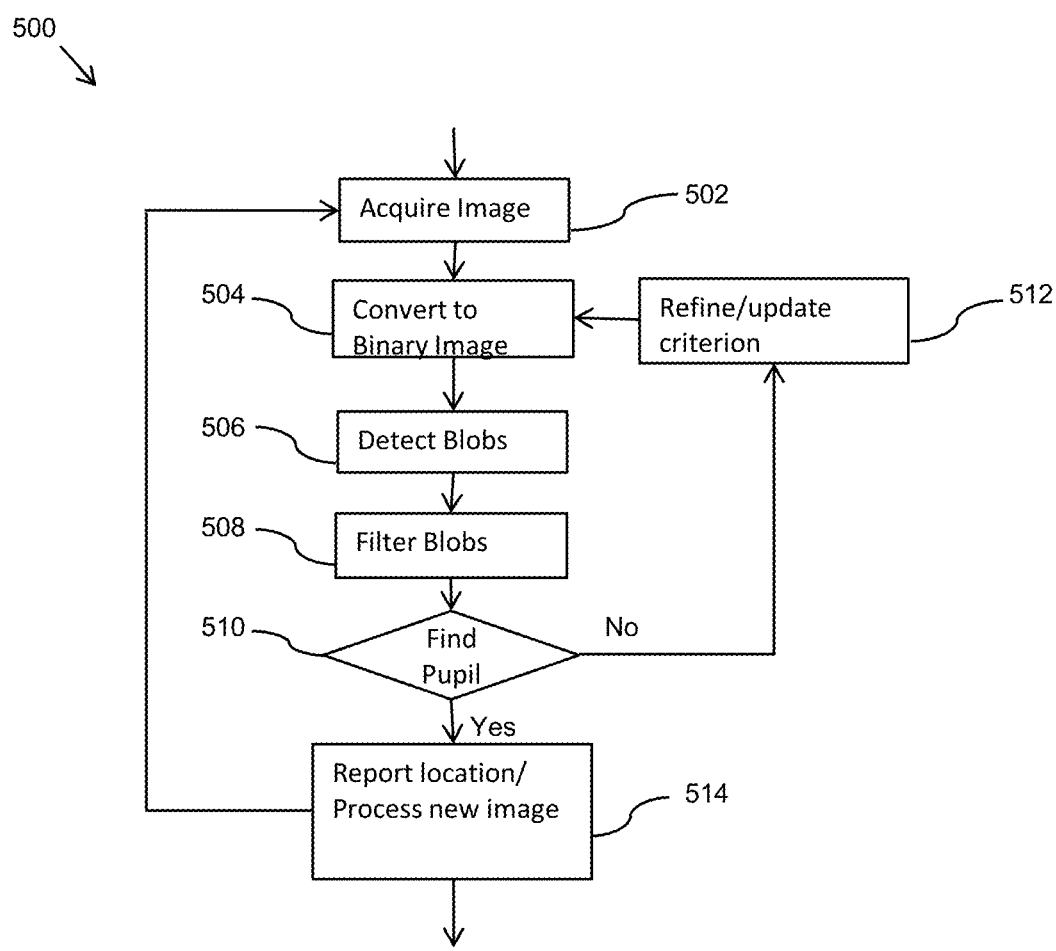
FIG. 5 illustrates an eye tracking algorithm.

An embodiment of an eye tracking algorithm 500 is illustrated in FIG. 5. In step 502, an eye camera, such as left eye camera 306L acquires an image of an eye of the user of the MVC. In at least one embodiment, the image is black and white. In step 504, the image is converted into a binary image in which all pixels are either black or white. The binary image conversion is performed by choosing a predetermined threshold and converting all pixels at or below the threshold to black, and all pixels above the threshold to white. The black and white image includes one or more "blobs" or black areas indicating possible locations of the pupil of the eye of the user. In step 506, a blob detection algorithm is performed to detect the blobs within the binary image. In step 508, a filtering algorithm is performed on the blobs to identify the blob that is the most likely candidate for the location of the pupil. In step 510, it is determined whether the pupil has been found. If the pupil has not been found, the procedure continues to step 512. In step 512, the criterion for converting the image to a binary image is revised and the procedure returns to step 504 in which the acquired image is converted to a binary image. The refining or updating includes choosing a new threshold for binary conversion. For example, if the chosen threshold results in too many pixels being identified as black, the threshold can be raised. If it is determined in step 510 that the pupil has been found, the procedure continues to step 514. In step 514, the location of the pupil is reported to the microprocessor 104, and the procedure returns to step 502 in which a new image is acquired. By determining the location of the pupil, the direction that the user of MVC is looking can be determined.

While the techniques illustrated in FIG. 5 can be implemented easily on a desktop or laptop computer, they will typically require too much processing power and battery consumption, and are not suitable for mobile devices such as smart phones. The complexity arises from the fact that there are too many candidate blobs (connected regions within the image frame) that have to be evaluated before the pupil is found.

In various embodiments, that complexity is eliminated or reduced by proper illumination of the eye surface and the setup of the camera. In at least one embodiment, one or more infrared LEDs are used to illuminate the eye surface of the user of the MVC. In a particular embodiment, the wavelength of the infrared illumination is between 820 nm and 950 nm. The one or more infrared LEDs allow obtaining an image of the user's eye under varying outdoor and indoor light conditions. Because little or no infrared light is reflected from the pupil, it will be seen as the darkest area in the image. As a result, an image that usually has a single blob is obtained. In at least one embodiment, an array of LEDs is used to illuminate the eye surface and corners uniformly. This allows very fast detection of the pupil location compared to existing schemes which are extremely CPU intensive which results in quick battery consumption.

In various embodiments, the illumination level is controlled at startup of the MVC and during calibration. At all times, the IR-LED power level is maintained significantly below the safe exposure level specified by standards. In at least one embodiment, the LEDs are modulated to reduce eye exposure by the infrared LEDs by periodically illuminating the eye of the user during the capturing of the eye image. In a simple embodiment, a duty cycle of 50% for infrared LED modulation is used for the periodic illumination of the eye which results in eye exposure being reduced by half. In still other embodiments, other desired duty cycles or periods may be used during eye tracking. For example, to use the MVC as a camcorder, the image frame should move gracefully. This means that the pupil location is not needed at the frame rate. If the pupil is tracked every second, then the eye exposure is further reduced by at least a factor of 30. It is also possible to alternate tracking the two eyes which reduces per eye exposure by another factor of two. In a particular embodiment, only one eye tracking camera is used for eye tracking at a time in order to reduce eye exposure to IR light.

For processing images taken by the eye tracking camera, the requirement of an image memory buffer is eliminated. As pixel values are passed by, the boundary (edges) of the pupil can be determined. If it is assumed that the pupil center is at the center of the boundary, the location of the pupil can be determined. In some embodiments, an option may be provided to fit an ellipse to the pupil boundary to provide a more enhanced procedure to track the location of the pupil. Examples of such procedure may be found in [1-3].

For image gathering, a black and white camera with a lens that has a wide enough FOV to cover the eye region is used in at least one embodiment. The camera generates gray scale images. For each user, the pupil will move in only a subset of the whole image frame. During initial setup of the MVC, this subset is determined with some added margin for error. In all subsequent processing, only that subset is processed. In some cameras, the camera can also be programmed so that only the desired sub-window is reported as the output image. Useless pixels are ignored to lower power consumption.

A common step in most image processing routines for eye tracking is to convert a gray scale into a binary image (black and white) by proper choice of a threshold voltage. An example of a processing an acquired image to produce a binary image including a pupil is illustrated in FIGS. 6a-6c. In FIG. 6a, a gray scale image 602 of an eye of the user of the MVC as acquired by an eye-camera is illustrated. FIG. 6b illustrates its corresponding histogram 604 and finding an optimum value for the threshold voltage 606 in order to determine the location of the pupil. FIG. 6c illustrates the resultant binary image 608 produced by applying the threshold voltage to the gray scale image 602 in a binary conversion procedure. With this approach, a single blob may be obtained in the binary image which is easy to process. FIG. 6c illustrates the result of an algorithm to locate the center of the pupil which is located at the intersection of line 610 and line 612. In a particular embodiment, alternating image frames of the eye tracking cameras are used to find the proper value of threshold voltage in order to convert a gray scale image into a binary image without the need to buffer the image data.

Figure 7:
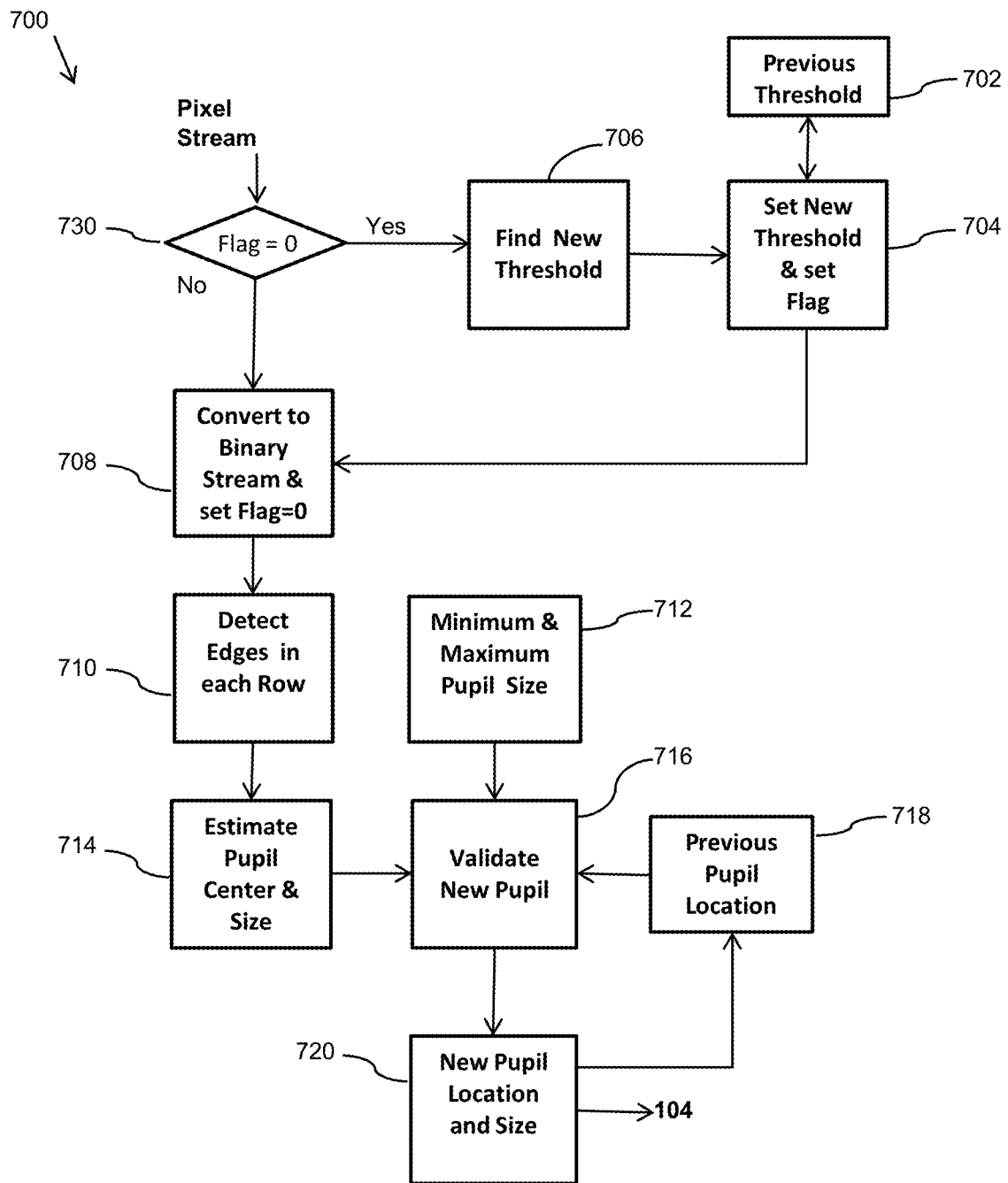
FIG. 7 illustrates an embodiment of a simplified and CPU-efficient algorithm for pupil detection which can be implemented in hardware.

FIG. 7 illustrates an embodiment 700 of a simplified and CPU-efficient algorithm for pupil detection which can be implemented in hardware without image processing routines. This approach relies on the fact that multi-IR-LED illumination of eye surface results in a single blob when the gray image is converted to binary. The embodiment includes a find threshold module 706, a convert to binary image module 708, a detect edges 710 (in one dimension as each data row is received), previous threshold value 702, set new threshold value 704, estimate pupil center and size 714, validate new pupil 716, minimum and maximum pupil size 712, previous pupil location 718, and location and size of new pupil 720. A control decision circuit 730 at the input finds the threshold value according to every other frame. The find threshold module 706 receives all pixel values and forms a histogram. It furthermore finds the location of the first minimum in the histogram data. The set new threshold level 704 receives the new threshold value and compares it to the previous value before it sets the threshold value level that is used by the covert to binary image module 708. Set new threshold level 704 also resets the flag value so that the next image frame will be processed for pupil location. The convert to binary image module 708 converts the digitized pixel value to a binary value one pixel at a time (serial processing). If the pixel value is less than threshold, it is set to zero; otherwise to one. The convert to binary image module 708 then sends the pixel data, the to the detect edge module 710.

The detect edge module 710 detects the edges of the binary image and outputs the edge information to the estimate pupil center and size 714. This estimate in fed to the new pupil 716 in which the estimate is questioned based on the constraints from the minimum and maximum pupil size 712 and previous location of pupil 718. The final pupil information is fed to the Scene Tracking Processor 104. The maximum pupil radius value is indicative of the maximum radius that a pupil can be expected to be in an image, and the minimum pupil radius value is representative of the minimum pupil radius that a pupil can be expected to be in an image. The max and min values may be used to discard erroneous estimates.

In a particular embodiment, an eye tracking algorithm employs the following steps: a) read-in all the pixel values; b) find their average value and form a histogram in a range between lowest and the average value; c) look for the first minimum after the peak to set a threshold voltage; d) use the said threshold to convert the next image into a binary on the fly; e) read-in the image values and record the boundary of the pupil; f) use the boundary values to find the pupil center; g) use the center and boundary values to find out if new pupil location is acceptable; and h) report the pupil center and the boundaries.

A Simpler Eye Tracking Approach

A second solution is even simpler than the one described in FIG. 7. The new approach does not require forming a histogram and finding a threshold, and converting the image into a binary. To achieve these, processing of an M×N image array is reduced into processing of two one-dimensional arrays of the lengths of M and N. In other words, digital image processing is reduced to digital signal processing. If the complexity of the image processing (2D) is of the N×N order, the signal processing approach has a complexity of the order N.

Assume the image I has M rows and N columns and form two vectors (data arrays): Row vector R and Column vector C. R has N elements and C has M elements. The i-th element of C is the minimum value of the i-th row of the image I. The j-th element of R is the minimum value of the j-th column of the image. Mathematically R and C can be written as:

$C(i)$=minimum value of $I(i,:)$, where $I(i,:)$ is the i-th row of image I, and $R(j)$=minimum value of $I(:,j)$, where $I(:,j)$ is the j-th column of image I.

In other words, R is the minimum-hold of the columns and C contains the minimum-hold values of the rows. Minimum-hold circuits can be implemented in hardware easily.

In a at least one embodiment, an eye tracking algorithm employs the following steps: a) form two minimum-hold row and column vectors out of the image data; b) smooth the two vector data using a low pass filter; c) take numerical derivative of each vector; d) find the center and boundaries of the largest and widest valley in each vector; e) use the center and boundary values to find out if data is acceptable; and f) report center coordinate as the pupil center and the boundaries as estimate of the size of pupil. In a particular embodiment, the low pass filter is a median filter.

Figure 8:
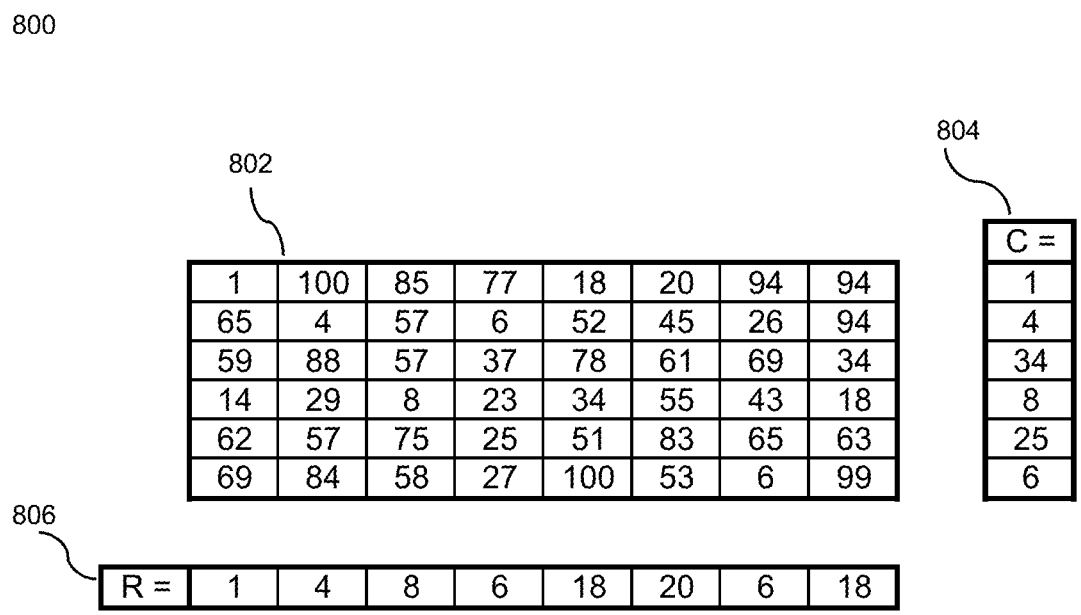
FIG. 8 illustrates a numerical example of a second algorithm for pupil detection which can be programmed into a camera on a chip module.

A numerical example of a second algorithm for pupil detection which can be programmed into camera on a chip is illustrated in FIG. 8. As an illustrative example, a matrix of 6 rows and 8 columns is shown in FIG. 8. The minimum values for each row and columns are also listed under C and R vectors.

Figure 9:
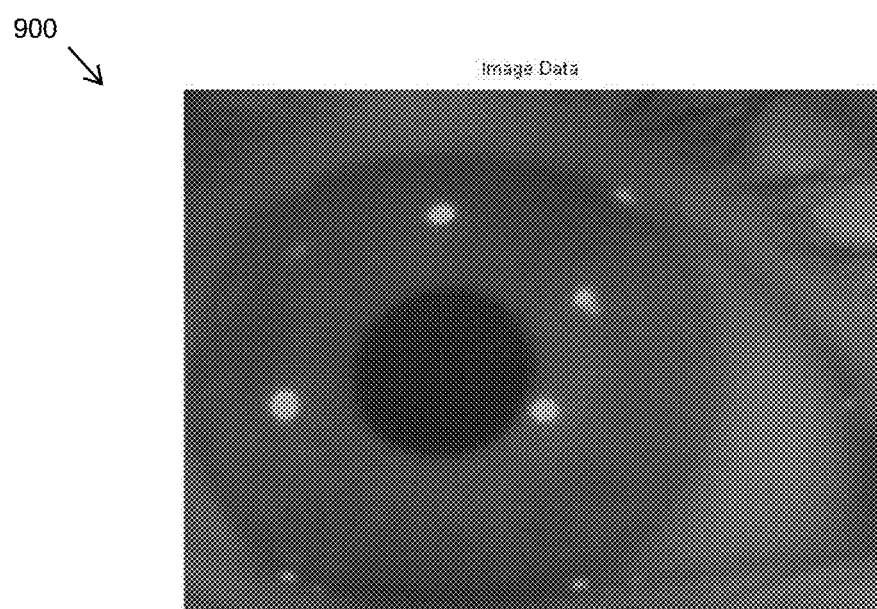
FIG. 9 illustrates an image of an eye that is illuminated with multi IR-LED.
Figure 10:
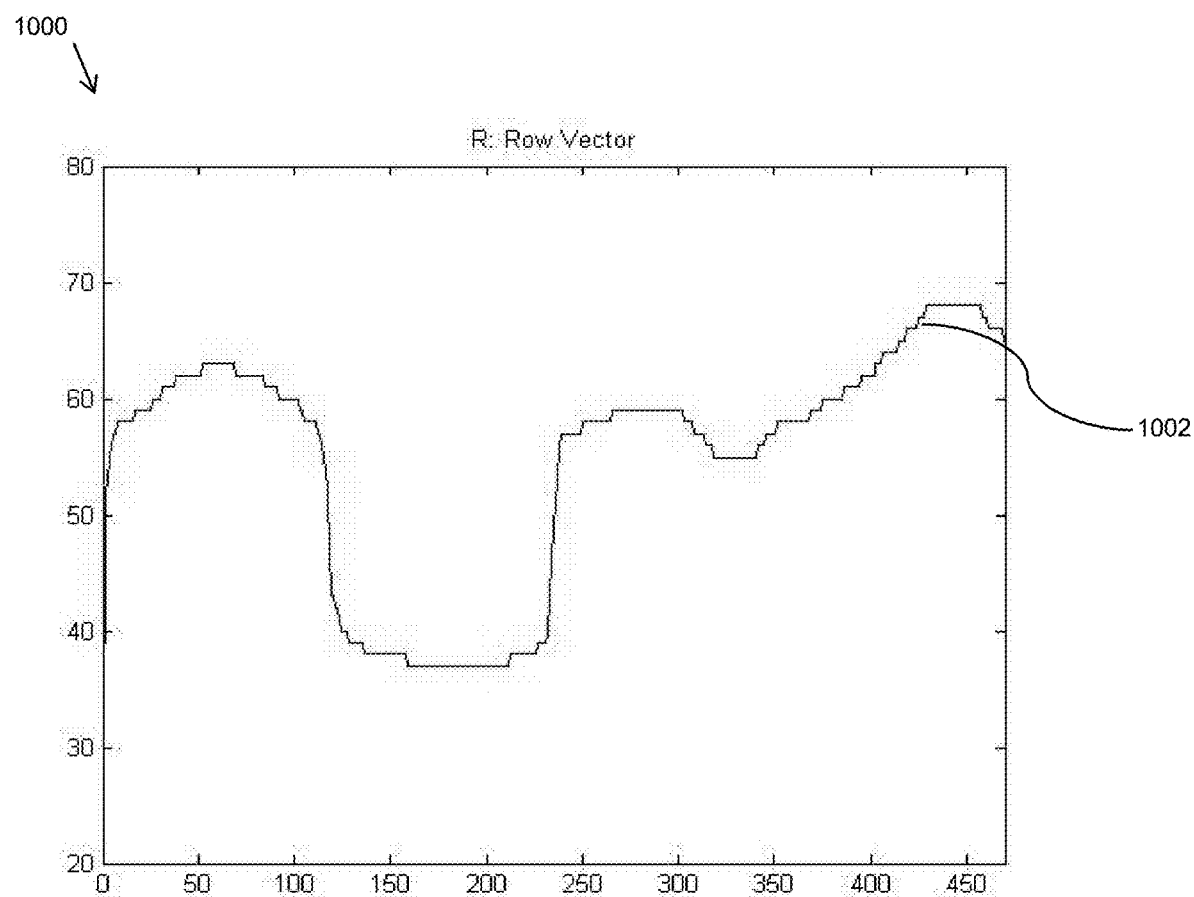
FIG. 10 shows the calculated Row Vector for the image shown in FIG. 9.
Figure 11:
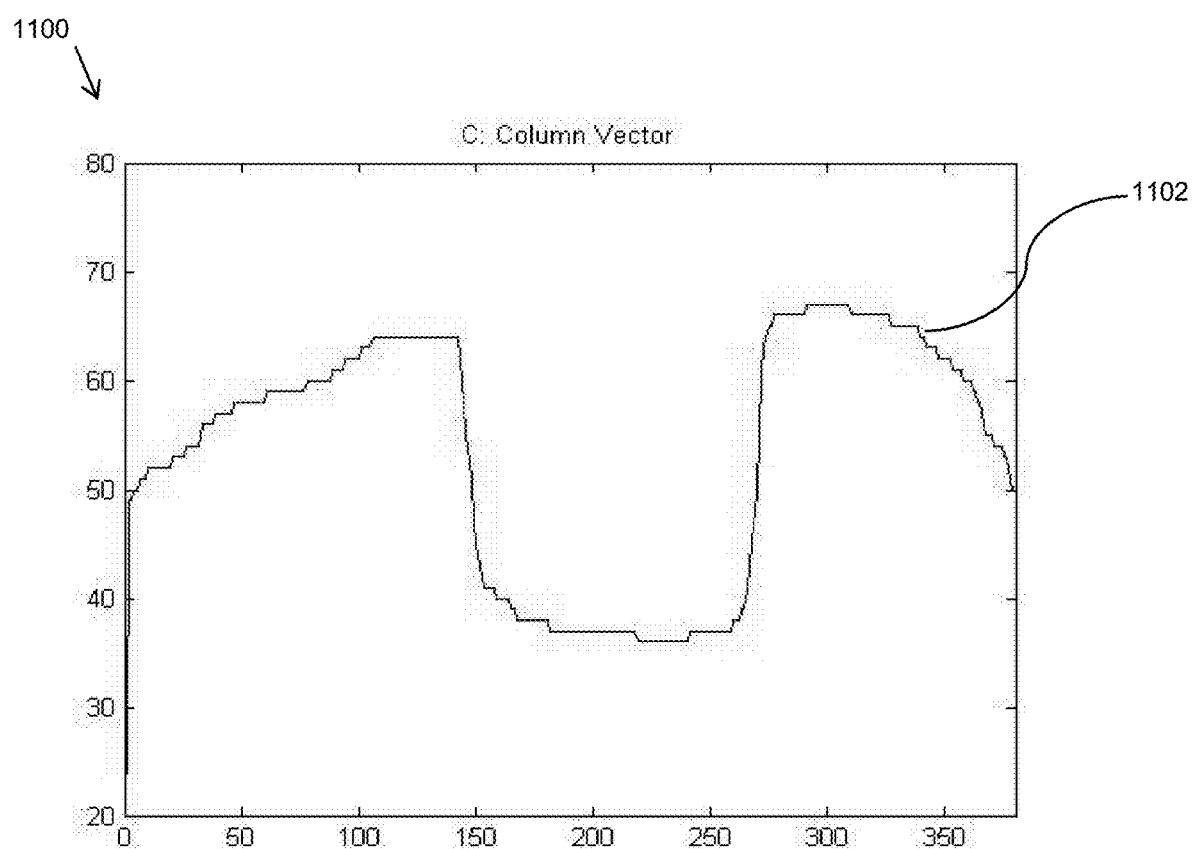
FIG. 11 shows the calculated Column Vector for the image shown in FIG. 9.

This technique is applied to a real eye image that was illuminated with six IR-LED. FIG. 9 illustrates an image of an eye that is illuminated with multi IR-LED. FIG. 10 shows the calculated Row Vector R 1002 for the image shown in FIG. 9 and FIG. 11 shows the calculated Column Vector C Vector 1102 for the image shown in FIG. 9, respectively, after being smoothed by a median filter. In at least one embodiment, a low pass filter may be used. The large dip in each plot corresponds to the boundaries of pupil and the center of each dip is the center of pupil in horizontal and vertical directions. The following additional array processing are steps utilized to find the coordinates of the pupil numerically.

Figure 12:
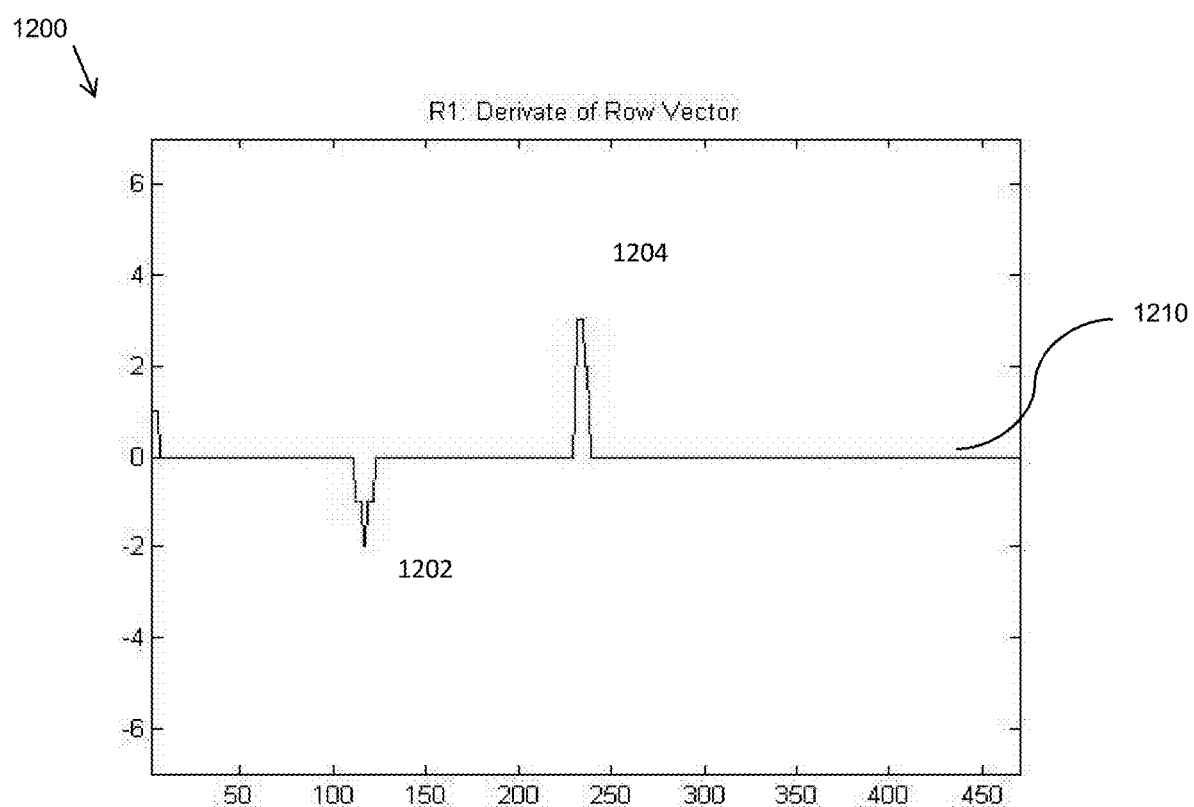
FIG. 12 shows that calculated derivative of the Row Vector.
Figure 13:
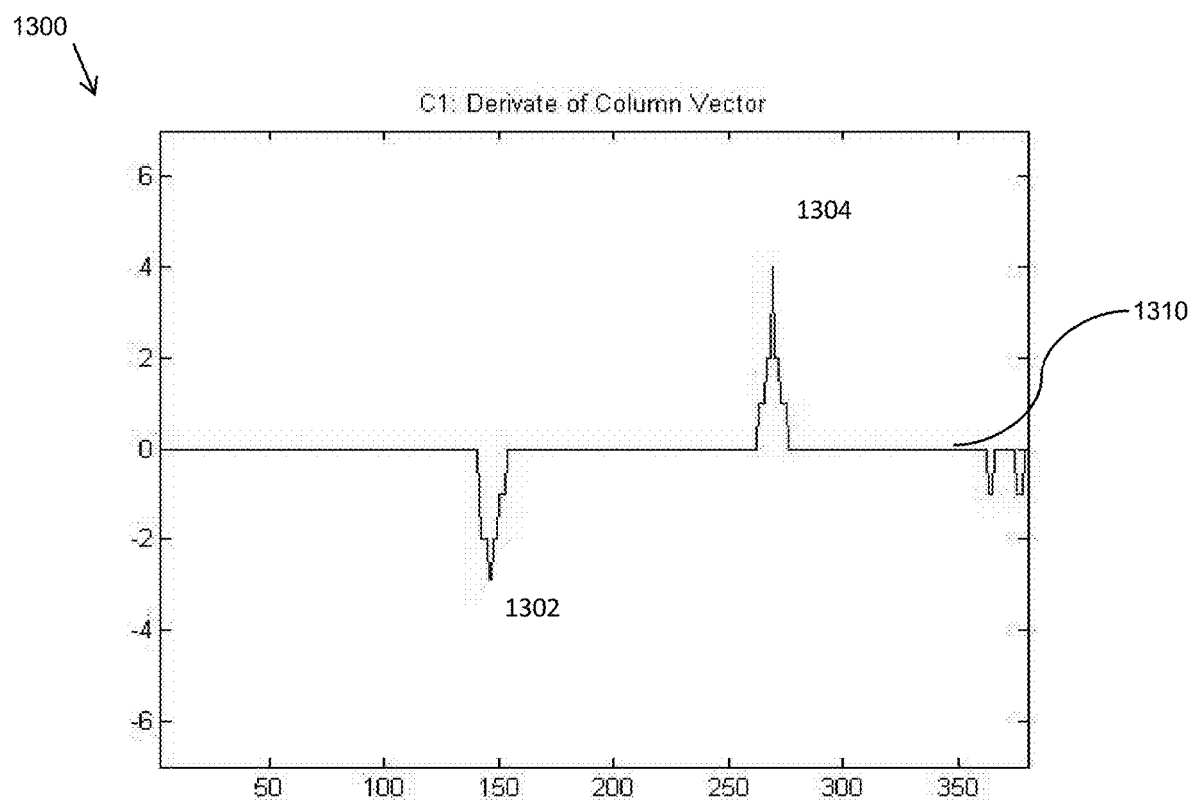
FIG. 13 shows that calculated derivative of the Column Vector.

First, the derivative of each array is found numerically to find the boundaries of the pupil in each direction (vertical or horizontal). The two derivative arrays are denoted by R1 and C1. For the image shown in FIG. 9, the calculated derivative of the Row Vector, R1 derivative vector 1210, and calculated derivative of the Column Vector, C1 derivative vector 1310 are shown in FIGS. 12 and 13, respectively. In FIG. 12, the two peaks 1202 and 1204 mark the horizontal boundary of the pupil. In FIG. 13, the two peaks 1302 and 1304 mark the vertical boundary of the pupil.

It should be noted that once R1 and C1 are calculated, there is no need for the data in R and C vectors. Therefore, R and C memory spaces can be reused for storing R1 and C1. In general there may be many small peaks on the R1 and C1 curves. These peaks have no useful information regarding the pupil location. Therefore, it is beneficial to smooth the derivative vectors before identifying the pupil boundary via the following three rules:

1. The signs of the derivatives on the boundaries of pupil are a negative local minimum followed immediately by a positive local maximum. In fact, for proper eye illumination, these minimum and maximum values are the global minimum and maximum.

2. The distance between the two boundaries must fall within the maximum and minimum size of pupil. These max and min values can be stored in a look up table for each user. In general, a default max and min values for pupil size can be set.

3. Midpoint of the two boundary points is location of the pupil center in that direction.

Figure 14:
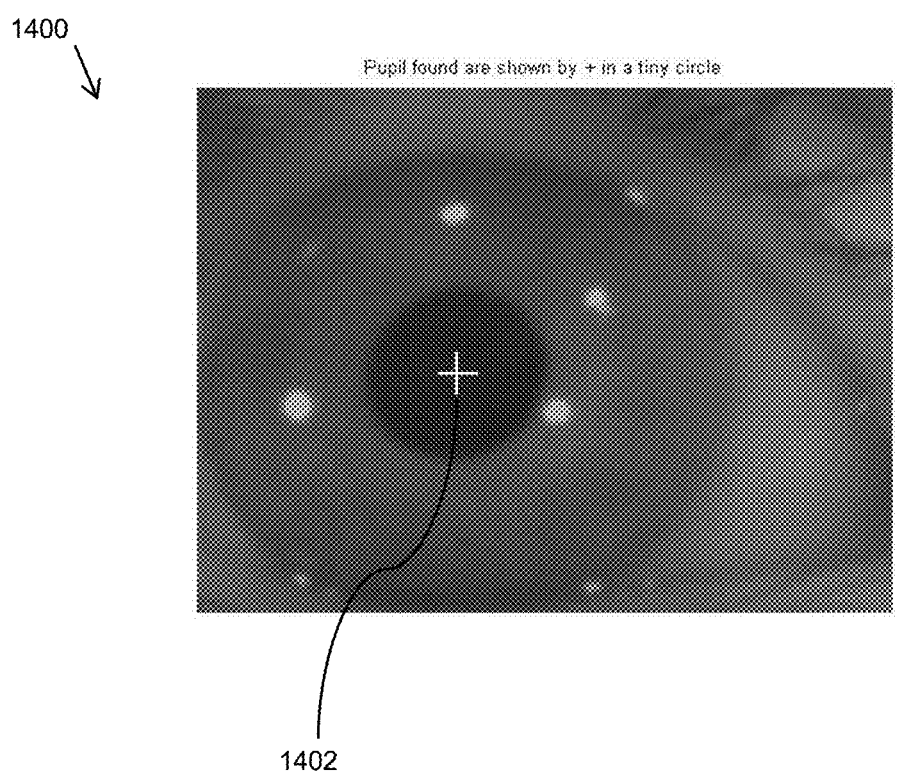
FIG. 14 shows the calculated location of the center of the pupil on the image.

The location of the pupil center 1402 calculated through this method is shown in FIG. 14 as superimposed on the original eye image.

Figure 15:
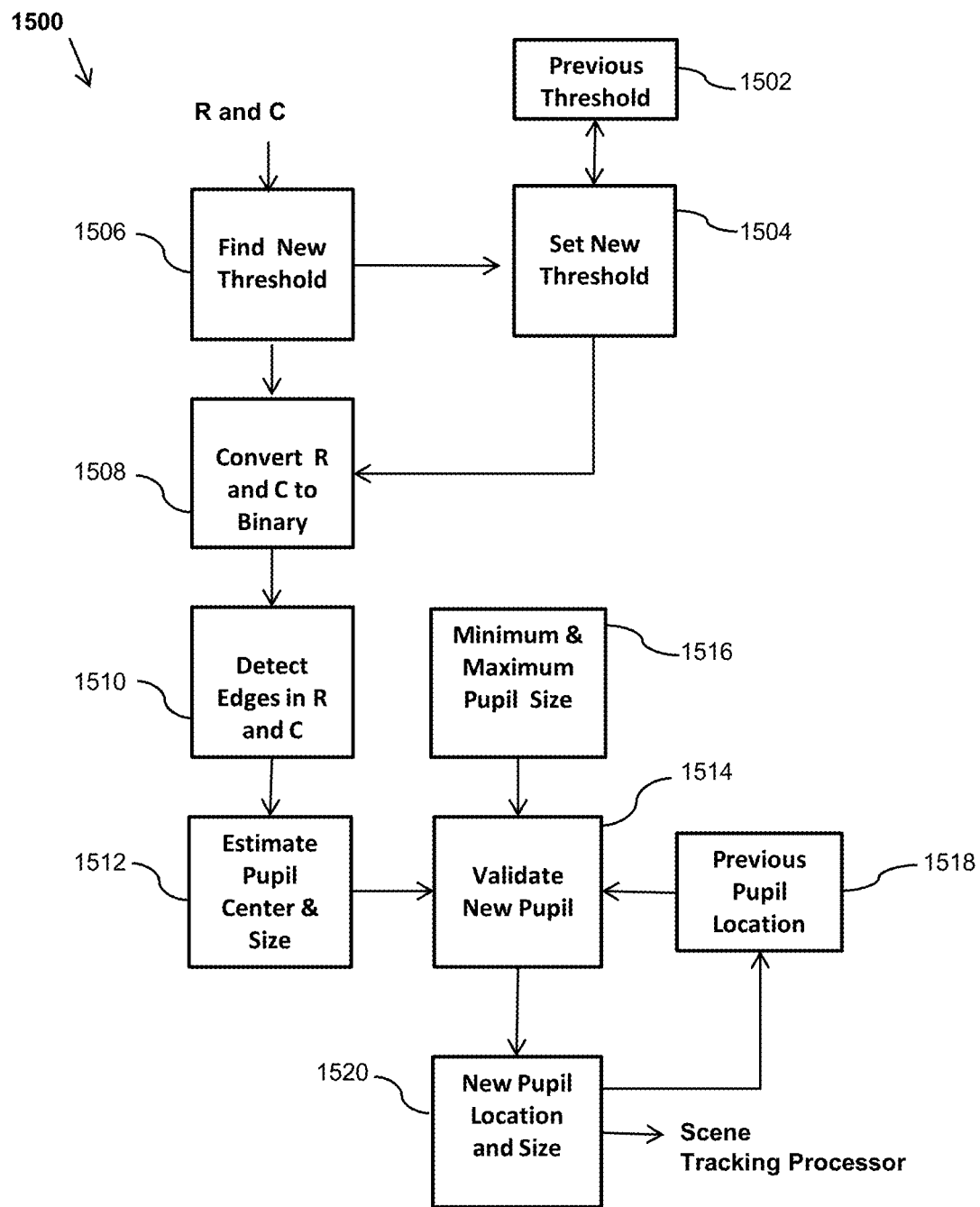
FIG. 15 illustrates an embodiment of a simplified and CPU-efficient algorithm for pupil detection which can be implemented in hardware.

Once the R and C vectors are known, there is a yet another simple approach to extract pupil coordinates from the two vectors. FIG. 15 illustrates an embodiment of a simplified and CPU-efficient algorithm for pupil detection which can be implemented in hardware as illustrated in the flowchart 1500. R and C vectors are the two inputs. In step 1506, a histogram for at least R or C is formed. From this histogram, a threshold value is found and is fed to Set New Threshold 1504. This Set New Threshold unit 1504 compares the new value with the old ones and if it is valid, it supplies that to 1508 to convert the R and C into binary vectors. Otherwise, no processing happens until a new threshold is provided to 1504. The binary R and C vectors are passed to 1510 and in this block the index of the leading and trailing edges are recorded and fed to 1512. In 1512, midpoints of the two edges are found and reported to 1514 as pupil location. The Validate New Pupil block uses inputs from Previous Pupil Location 1518 and allowed Minimum & Maximum Pupil Size 1516 to confirm the new pupil location. This data is reported to New Pupil Location and Size 1520 which in turn feeds that data to the Scene Selection Microprocessor 104.

With a minor change in criteria the above algorithm can be used to locate the reflection points due to the IR-LEDs within the image. Specifically, rather than looking for the darkest part in the eye image, brightest spots are found through maximum-hold vectors (minimum-hold is used to find the pupil in the eye image). A number of pieces of information can be extracted from the locations of the IR-LEDs. For example, the number of illuminating LEDs can determined. In addition, existence of the bright spots due to reflections and the dark spot due to the pupil indicate that the user is wearing the camera. Given that the locations of the LEDs are known within the eyeglasses frame and given the average curvature of human eye surface, the locations of the LED images on the eye surface can be used to estimate the distance of the frame from the eye surface.

In embodiments of the design described herein, stereo eye tracking is used to independently track each eye. When the eyes focus on a scene, each eye axis makes a different angle with respect to the frame. With this information, which is a basis of triangulation technique (knowing the length of the base and the two angles that have a common side), the location of the third corner of the triangle corresponds to the distance of the user from the scene of interest.

Implementation of Presented Eye Tracking Approaches

Camera chips perform a number of processing tasks on the pixel values before an image is provided at the output of the device. These tasks are collectively called "image pipeline" and they include: black clamp, lens distortion compensation, fault pixel interpolation, white balance, CFA (color filter array) interpolation, gamma correction, color space conversion, edge enhancement, auto-exposure and image conversion and compression.

The three algorithms that were presented for eye tracking require much less computation resources and memory than the tasks that are currently performed on camera chips. Additionally, for eye tracking, many of those tasks might be skipped. The conclusion is that the existing firmware on camera chips can be modified so that all the processing is done on the camera chip. This results in a power saving and compactness of the MVC compared to the case where processing occurs outside the camera chip. In at least one embodiment, the eye tracking cameras are programmed to execute the eye tracking algorithms described herein directly and report pupil location to the Scene Camera Microprocessor 104. In a particular embodiment, the eye tracking cameras may be set to down-sample the image data before it is transferred to the Scene Camera Microprocessor 104. Furthermore, since the only data that the camera chip needs to send to the Scene Camera Microprocessor 104 is the pupil coordinate, the same low speed communication and camera control channel such as I2C can also serve as eye tracking data transmission channel.

When the eye images are needed at the electronic box, it is preferred to transmit the image data via a two wire transmission line such as a twisted pair. The data format may be analog (such as NTSC) or serial (such as BT565).

High Resolution Imaging

In the foregoing discussion, embodiments of a dynamic and hands-free Mind-view Video Recorder (MVC) are described. In one implementation of that device a pair of eyeglasses' frame is modified to enclose a lens and CCD or CMOS and its associated electronics. To be practical, the mind view recorder should be lightweight, easy to wear and have a non-distractive appearance, i.e., be aesthetically pleasing. To achieve this goal, it is desired that the camera module (lens and the detector) be as small as possible. One way to lower the size is to use smaller lenses and detector chips with lower pixel counts. However, this degrades the resolution and quality of the video. In the following discussion, embodiments of various techniques and devices are described to obtain high resolution video using small optical lenses or camera modules.

These embodiments can be classified into two groups: spatial or temporal techniques. In both groups, one wide angle camera images the whole scene of interest. It is this image that needs its resolution to be increased. A second camera is also used to acquire additional detailed information about the scene. The images of this second camera are used to enhance the images of the first camera or are used directly when the user's gaze-point falls within the FOV of this second camera. In the spatial technique method, the second camera takes images of a subset of the whole FOV with an increased resolution. In the temporal technique, the second camera has the same FOV as the first camera but it is samples the scene at the same or higher frame rate.

Approach #1: Spatial Techniques

One way to achieve higher resolution for a fixed lens and image sensor is to use Super Resolution (SR) techniques [4-12]. Bandwidth extrapolation is one of the well-known SR techniques [8-10] which enforces constraints on the image in space and spatial frequency domain in an iterative manner. The mathematical basis of bandwidth extrapolation has been known for about three decades [8-10] and it relies on two fundamental theorems described in [8]. These two theories state that [8]:

"Theorem 1. The two-dimensional Fourier transform of a spatially bounded function is an analytic function in the frequency plane.

Theorem 2. If an analytic function in the frequency plane is known exactly in an arbitrarily small (but finite) region of that plane, then the entire function can be found (uniquely) by means of analytic continuation."

The key determining factor for successful and practical implementation of SR is to characterize the underlying analytic function even in a small region but as much as possible. In fact, the resolution improvement is limited to the accuracy of the extra information that are gathered about the image. If the function is known exactly in a very small area, the image can be recovered precisely. Next a resolution enhancement implementation based on the stated theorems is presented.

In one design, a wide angle camera takes images of the whole FOV of interest (central and peripheral view). This camera is referred to as a Low Resolution (LR) camera. The objective is to increase the resolution of the images taken by this LR camera. To achieve this, a portion (subset) of the whole FOV is imaged with a second but higher resolution camera having a narrower field of view. This High Resolution (HR) image increases the information about the scene and is utilized to increase the resolution of the lower resolution (LR) images. This arrangement is a unique practical and computationally efficient implementation of the above two theorems. In a particular embodiment, both the wide and narrow angle cameras use the same kind of image sensor.

As a numerical example about the magnitude of resolution enhancements, consider two cameras that have the same image sensors but one have a field of view that is four times larger than the other one (2× horizontal and 2× vertical). Furthermore, assume that each image sensor has 4 million pixels (2000×2000) and these cameras are used to record 720p HD video that requires 1 million pixels per frame. Through pixel binning, the narrow angle HR camera can capture a subset of the scene at various binning levels. For example, for the same binning on both camera (four to one-to convert 4 million pixels into 1 million), the resolution of the narrow angle image is four times higher. This additional information can be further increased by another factor of four (total of 16× resolution increase) if only select 1 million neighboring pixels on the high resolution camera around any area of interest are selected. This is the same as selecting a sub-window on the HR camera without any binning. Of course, this sub-window can move along the image sensor area as needed. So from theory for the above example, the resolution of the LR-camera can be increased by a factor of 16. This is equivalent to optical zooming for the wide-angle scene. Such optical zooming cannot be achieved via any point and shoot camcorders.

Any imaging system adds distortion and noise to the real image. The common term for image distortion is blurring and image deblurring is an inverse problem. There are a large number of academic papers that describe how to solve such problems [13-17].

Depending on the Point Spread Function (PSF) of the LR and HR lenses, there are two methods that can be used to enhance the LR image. The PSF of standard lenses is spatial-variant. For such lenses, methods such as those described in [13-14] can be used. However, with the help of the HR camera, additional and detailed information about the scene leads to better performance with less numerical computations. In the case of MVC cameras, the PSF of the utilized lenses as well as the characteristics of the image sensors in terms of pixel shape, size, fill factor and noise are measured and known. With the knowledge of PSF and noise, even simple deconvolution techniques can do a decent job in improving the resolution of the LR image. Of course, the additional high resolution images of portions of the whole FOV which can be used to test the accuracy of the result.

In contrast to standard camera lenses, wavefront coded lenses [18-21] have a spatially invariant PSF. This allows the use of simpler techniques based on inverse problems to enhance the LR images. In a particular embodiment, both the wide angle and the narrow angle cameras utilize wavefront coded lenses to extend the depth of focus. Given that the PSF's of both camera lenses are space invariant (and can be known or measured) and given that both cameras use similar image sensors (same hardware and software), the LR image can be treated as the "blurred" version of the scene (and the HR image). The task then becomes to "deblur" the LR image with the help of HR images that are collected by the HR camera. It should be noted that the two LR and HR cameras are placed within the same solid eyeglasses frame and hence the only difference between their coordinates is a lateral displacement when the two cameras are coplanar. It is also possible that the optical axes of the two cameras are not exactly parallel and there is a small convergence angle. In various embodiments, image projection and coordinate transformation is used to make images of the wide and narrow angle cameras into the same Cartesian coordinate. Image projection and displacement has been discussed in many computer vision textbooks. In any event, with the help of image registration techniques [22-24], the two images have the same coordinate before they are processed. In various embodiments, image registration techniques are used to transfer one camera's coordinates to the other camera. Examples of image registration techniques include Landweber technique, Block-Matching technique, and Fast Fourier Transform (FFT) technique.

In a particular embodiment, image deconvolution techniques are used to estimate the blurring function of the wide-angle camera with respect to the narrow-angle high resolution camera. In another embodiment, image deblurring techniques are used to estimate the blurring function of the wide-angle camera with respect to the narrow-angle camera. In still another embodiment, inverse formulation is used to estimate the blurring function of the wide-angle camera with respect to the narrow-angle camera. In various embodiments, camera characteristics are stored in a look up table and the look up table is used by the image processing techniques to increase the resolution of the LR image.

Figure 16:
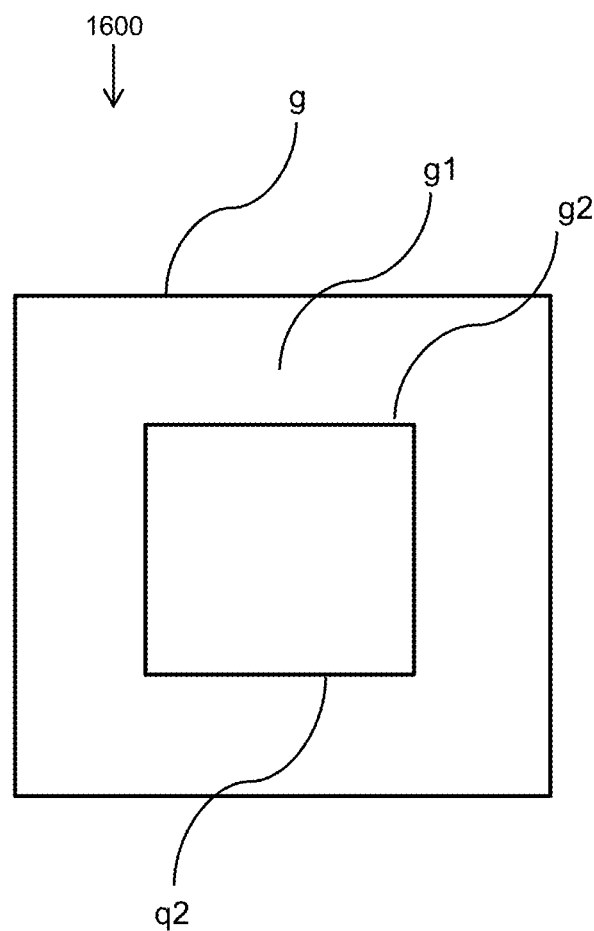
FIG. 16 shows the relative field of views captured by the two wide and narrow angle cameras in which the narrow angle camera captures a high resolution image (q2) of a subset of the wide angle view camera (g)

FIG. 16 shows the relative field of views captured by the two wide and narrow angle cameras in which the narrow angle camera captures a high resolution image (q2) of a subset of the wide angle view camera (g). In FIG. 16, the wide angle LR image is denoted by g where g=g1+g2. The true high resolution version of the same scene is f where f=f1+f2 and g1 and g2 are the low resolution images of f1 and f2, respectively. The HR camera records the area denoted by q2 (after image registration and translation). Assuming that the composite blurring functions h1 and h2 relate f and g, and q2 and f2 through convolution operation (g=h1*f and q2=h2*f2), then, g2=h1*f2.

To increase the resolution of the first camera to the level of the second camera, it is assumed q2=f2. With this assumption and via various inverse problem techniques, h in g2=h*q2 can be found because both g2 and q2 are known and measured, and the noise and distortion of both cameras are known. In the above expressions, the noise terms were ignored to describe the approach.

Figure 17A:
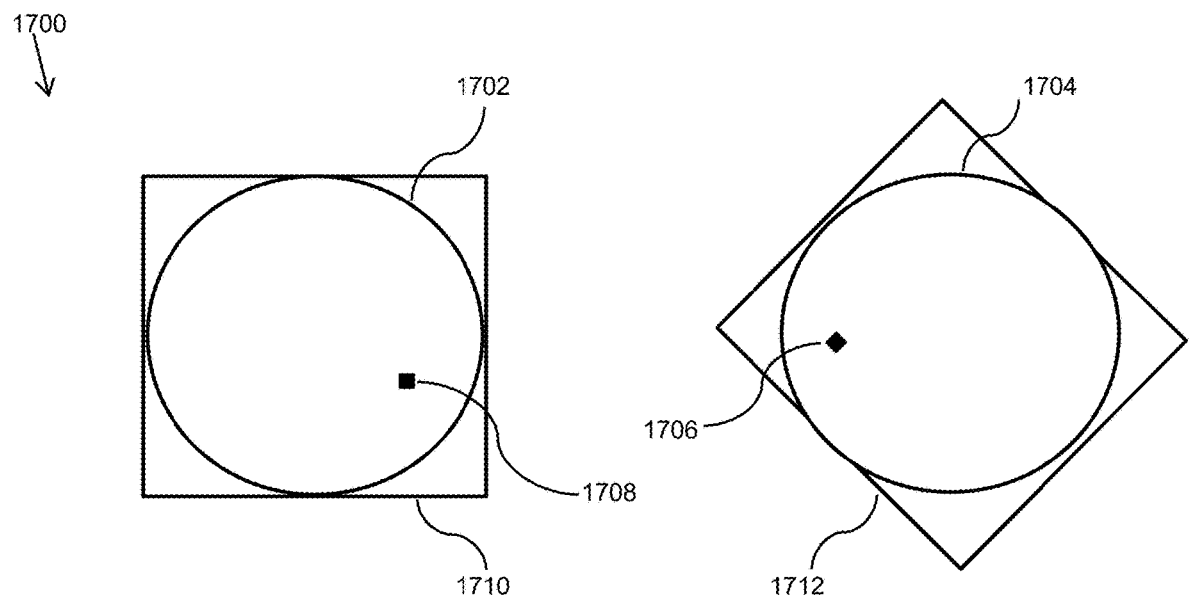
FIGS. 17a and 17b show two methods to achieve higher resolution sampling of the field of view through orientation diversity (17a) and via orthogonal orientation of rectangular pixels (17b)
Figure 17B:
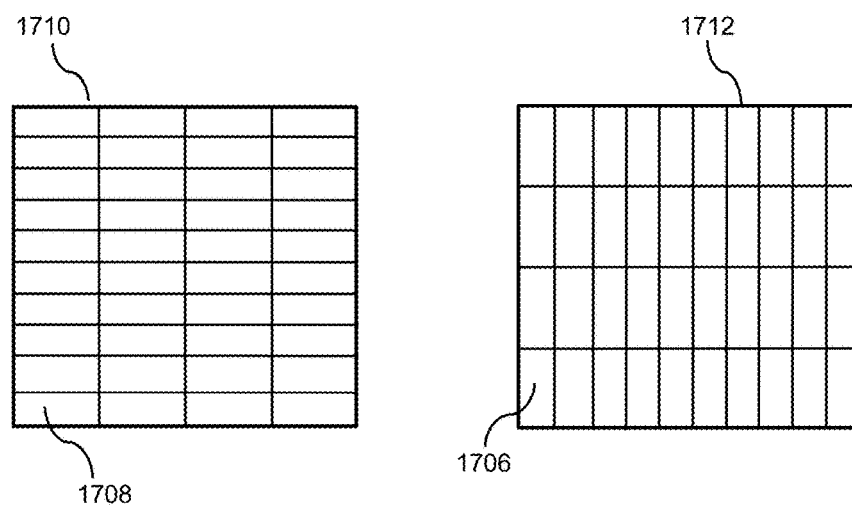

A special case of the spatial approach occurs when the second camera has the same FOV and image sensor as the first camera. Even in this case, a higher resolution image of the scene is obtained by proper positioning of the second image sensor with respect to the first one. The trick is to make the second camera sample the scene with minimum overlap with pixels of the first camera. FIGS. 17a and 17b show two configurations to achieve higher resolution sampling of the field of view through orientation diversity (FIG. 17a) and via orthogonal orientation of rectangular pixels (FIG. 17b). For example, the second image sensor may be rotated by 45 degrees with respect to the first image sensor if the pixels have a square shape (FIG. 17a). While the two image sensors still have similar electronic characteristics, their pixels never overlap. In the case of rectangular image pixels, the second image sensor will be rotated by 90 degrees with respect to the first sensor for maximum image enhancement. In fact, a good combination is having rectangular pixels with aspect ratio of 2:1. In this case, one camera samples the scene in horizontal direction and the other in the vertical direction. By combining the two images, total image resolution is doubled compared to either camera. An additional factor of two resolution improvement can be obtained through iterative bandwidth extrapolation technique.

In FIGS. 17a and 17b, the image sensors 1710 and 1712, respectively, were chosen to have square shapes with dimensions in such a way to collect all the light from the image gathering lenses. Hence, for a given lens, the configurations shown in FIG. 17a and FIG. 17b cover the maximum FOV with 100% light gathering efficiency. For the reference, the light gathering efficiency in a typical consumer grade camcorder with a fixed lens is 54%. In others words, about half of the FOV the lens collects is not used converted to an image.

In the cases described in FIGS. 17a and 17b, the two scene cameras have identical wide angle lenses and the image sensors are also identical but were positioned differently with respect to the scene. An additional configuration is obtained when the two image sensors are positioned in the same way with respect to the scene however one of the cameras is color and the other one is black and white (B&W). Since the B&W camera does not use any color filter, it has a higher signal to noise ratio and resolution. Furthermore, it does not suffer from numerical artifacts due to interpolation that is required to estimate missing color values at each pixel. By combining the images due to the two cameras, a color image is obtained that has a better resolution than the color image due to the color camera alone.

In various embodiments, the MVC utilizes eye tracking such as that described herein to choose a subset of the total FOV that the user is gazing at for resolution enhancement. Therefore, the LR camera can operate without any binning to record a higher resolution of the scene and only this subset needs to be enhanced. Also, many times the images from the HR camera (narrower FOV) can be used directly without any need for image registration or enhancement when the scene of interest is a subset of FOV of the HR camera. In a particular embodiment, the eye tracking apparatus is also embedded within the same eyeglasses frame that houses the video recording cameras. In various embodiments, the eye tracking unit also provides an estimate of the distance of the object from the cameras. In a particular embodiment, the object distance is estimated via triangulation applied to the scene recording cameras. In still other embodiments, the estimated distance is used to set the zoom level of the images to that of a normal human eye.

Figure 18:
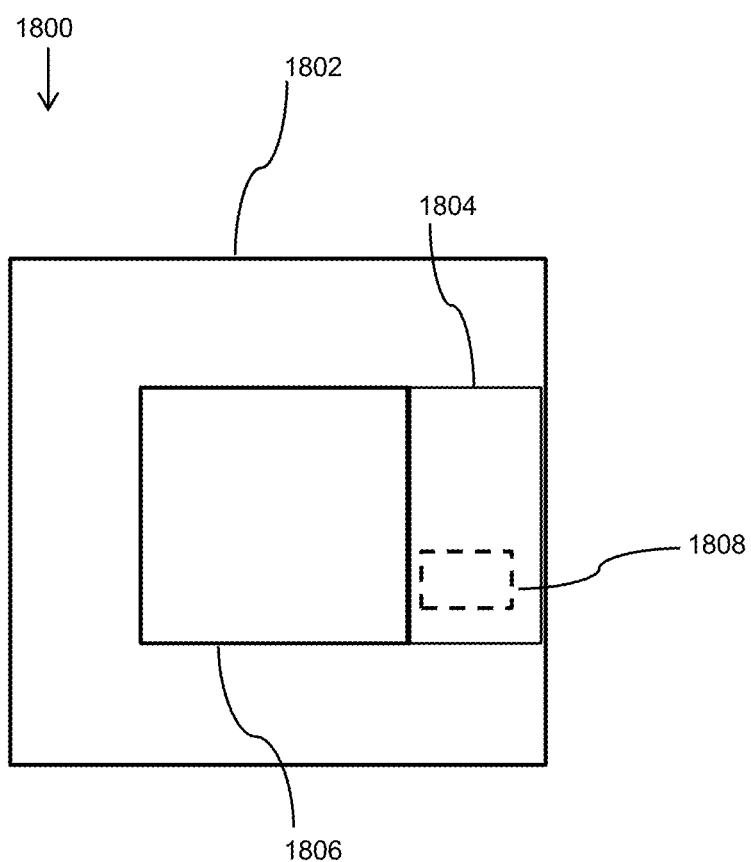
FIG. 18 illustrates a scene of interest with respect to the field of view of two cameras in which image data from the high resolution area N will be used to increase the resolution of the area denoted by A.

FIG. 18 illustrates a scene of interest with respect to the field of view of two cameras in which image data from the high resolution area N will be used to increase the resolution of the area denoted by A. Referring to FIG. 18 and its notations, when an area such as 1808 outside the FOV of HR camera 1806 is of interest, only a smaller subset of 1802 such as 1804 can be chosen in conjunction with 1806 for resolution enhancement. This lowers the amount of required computation significantly. Additionally, the size of the HR area 1806 is larger than 1804. This further reduces the required computations.

For completeness, it is possible to sample the wide angle FOV with more than one HR camera as shown in FIG. 19a-19c. FIGS. 19a-19c illustrate alternative configurations for high resolution sampling of whole field of view via more than one camera wherein FIGS. 19a, 19b and 19c five, three and two cameras, respectively, are used to sample the FOV of interest. In FIG. 19a, portions of the desired FOV 1902 are sampled by five HR imagers with FOVs marked by 1904a, 1904b, 1904c, 1904d and 1904e. In FIG. 19b, only three cameras with FOVs of 1906a, 1906b and 1906c were used to sample the total FOV 1902. FIG. 19c illustrates an embodiment with only two cameras to sample the FOV 1902. The two cameras FOV are denoted by 1908a and 1908b, respectively.

In FIG. 20, two configurations are presented that utilize only high resolution cameras to cover the desired FOV 2002. FIGS. 20a-20c illustrate an embodiment of a four-camera high resolution camera configuration to cover the whole field of view directly in which in FIGS. 20a and 20b the left and right camera modules FOV and their overlap are shown, and in FIG. 20c the net FOV with redundancies are shown. FIG. 20a shows the total FOV 2002 as well as the FOV of the left camera modules 2004L and 2006L. FOV of the right camera modules 2004R and 2006R are shown in FIG. 20b. In FIG. 20c, it is shown how the total FOV 2002 is covered by the four cameras.

FIG. 20d illustrates an embodiment of a two high resolution camera solution to cover the entire field of view of interest. In this case, the total FOV 2002 is covered by two cameras (one camera on each side of the frame) with fields of view marked by 2004L and 2004R. In the discussed configurations in FIGS. 20a-20d, the overlaps between the FOV of the various cameras is intentionally introduced to ease transitions from one camera to any other.

The solutions presented in FIGS. 20a-20d require less post-processing because all the cameras are high resolution (HR). Consequently, only one camera at a time needs to send images to the Scene Selection Microprocessor 104. The other one or three cameras go on standby mode to reduce power consumption. Still super resolution techniques can be applied to the images to further increase their resolution beyond the resolution of the image sensor of the cameras.

Approach #2: Temporal Techniques

There are a large number of academic papers under resolution enhancement and super-resolution in which multi low resolution images are used to generate a single high resolution image. A common approach is to use many frames from a low resolution (LR) video. In essence, these various frames are images of the same scene with random sub-pixel shift with respect to each other. A high resolution grid is formed and the LR frames are "registered" and placed on it before the high resolution image is constructed [4-7, 12].

Figure 21A:
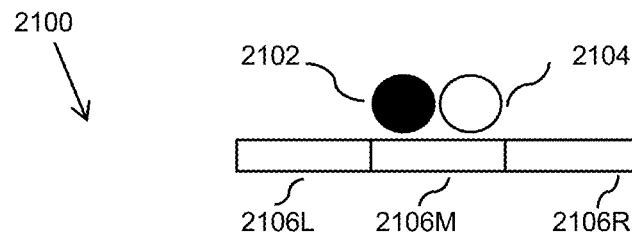
FIGS. 21a-21d illustrate graphically the concept of super resolution image enhancement via sub-pixel image shift across the image sensor.
Figure 21B:
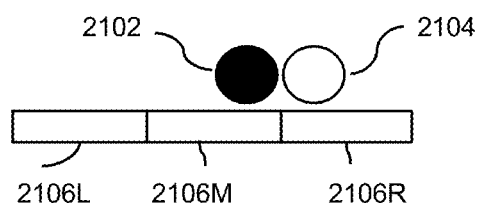
Figure 21C:
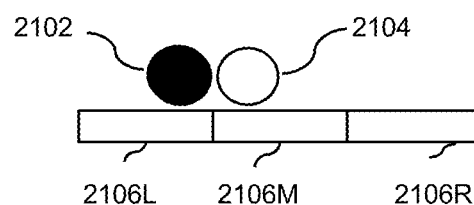
Figure 21D:
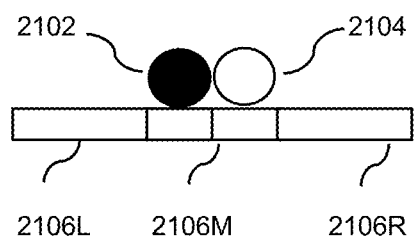

FIGS. 21a-21d illustrate graphically the concept of achieving super resolution image enhancement via sub-pixel image shift across the image sensor. Starting in FIG. 21a, images of two points 2102 and 2104 are detected by the same pixel 2106M. This means that those two points cannot be seen separately. In FIGS. 21b and 21c, it is shown by lateral displacement of the image across the neighboring pixels by a distance of a half-pixel, the two points can be distinguished from each other. In FIG. 21b, only 2102 object is detected by 2106 pixel whereas in FIG. 21c, only the 2104 object is seen by the 2106M pixel. The situations depicted in FIGS. 21a-21c can be expressed mathematically using three linear equations with three unknowns which has a unique solution. As shown in FIG. 21d, this demonstrates that through the half-pixel shift, the geometrical resolution of the image sensor has been increased by a factor of two, as if the 2106 pixel consisted of two half-sized pixels. This technique is useful because there is a trade-off between reducing the pixel size and image quality. At the optimum pixel size, by lateral displacement of the image over the image sensor, the resolution of the imaging device is increased. Of course, image processing is needed to "register" those additional images and convert them into a single but higher resolution image.

In a various embodiments, a second camera includes one or more devices or configurations to shift an image collected by a lens across the image sensor by a distance less than a dimension of the image sensor pixel. In particular embodiments, the distance of the shift may be a length of a pixel, a width of a pixel, or a diameter of a pixel.

Figure 22A:
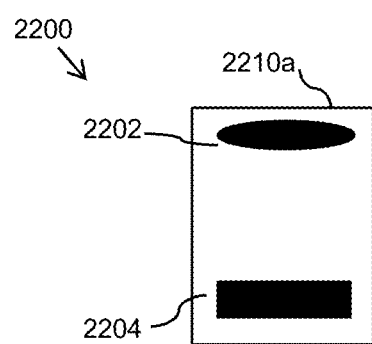
Figure 22B:
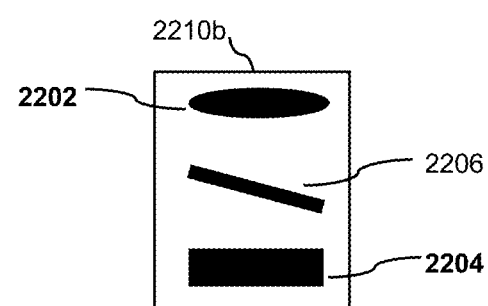
Figure 22C:
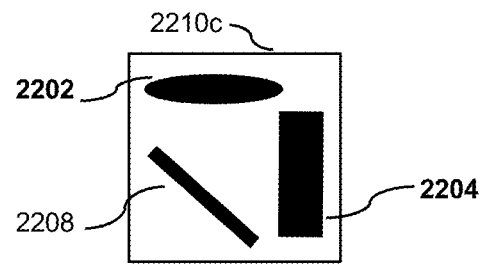

In the temporal approach, configurations and designs are used in order to capture a fixed number of sub-pixel-shifted images of the scene per each frame of the LR camera. For all the reported cases in this section, two wide-angle cameras are used. FIGS. 22a-22c depict embodiments of two imaging configurations to shift an image across an image sensor in which FIG. 22a shows a standard configuration for a lens and an imaging device, and FIG. 22b and FIG. 22c illustrate the key additional hardware to achieve image steering. One camera has a standard configuration as shown in FIG. 22a and is denoted as LR camera. This standard camera 2210a consists of two parts: a lens 2202 and an image sensor 2204. For the second camera, there are two possible implementations that are shown in FIGS. 22b and 22c to achieve such sub-pixel shift. In FIG. 22b, a movable transparent glass-plate 2206 is introduced between the lens 2202 and the image sensor 2204. In FIG. 22c, a micromechanical mirror 2208 reflects the light from the lens 2202 onto the image sensor 2204. By adjusting the amount of the tilt of the either glass-plate 2206 or mirror 2208, the amount of sub-pixel shift across the pixels can be controlled. In a particular embodiment, the movable or tiltable mirror 2208 is a micro-electro-mechanical device.

Figure 23:
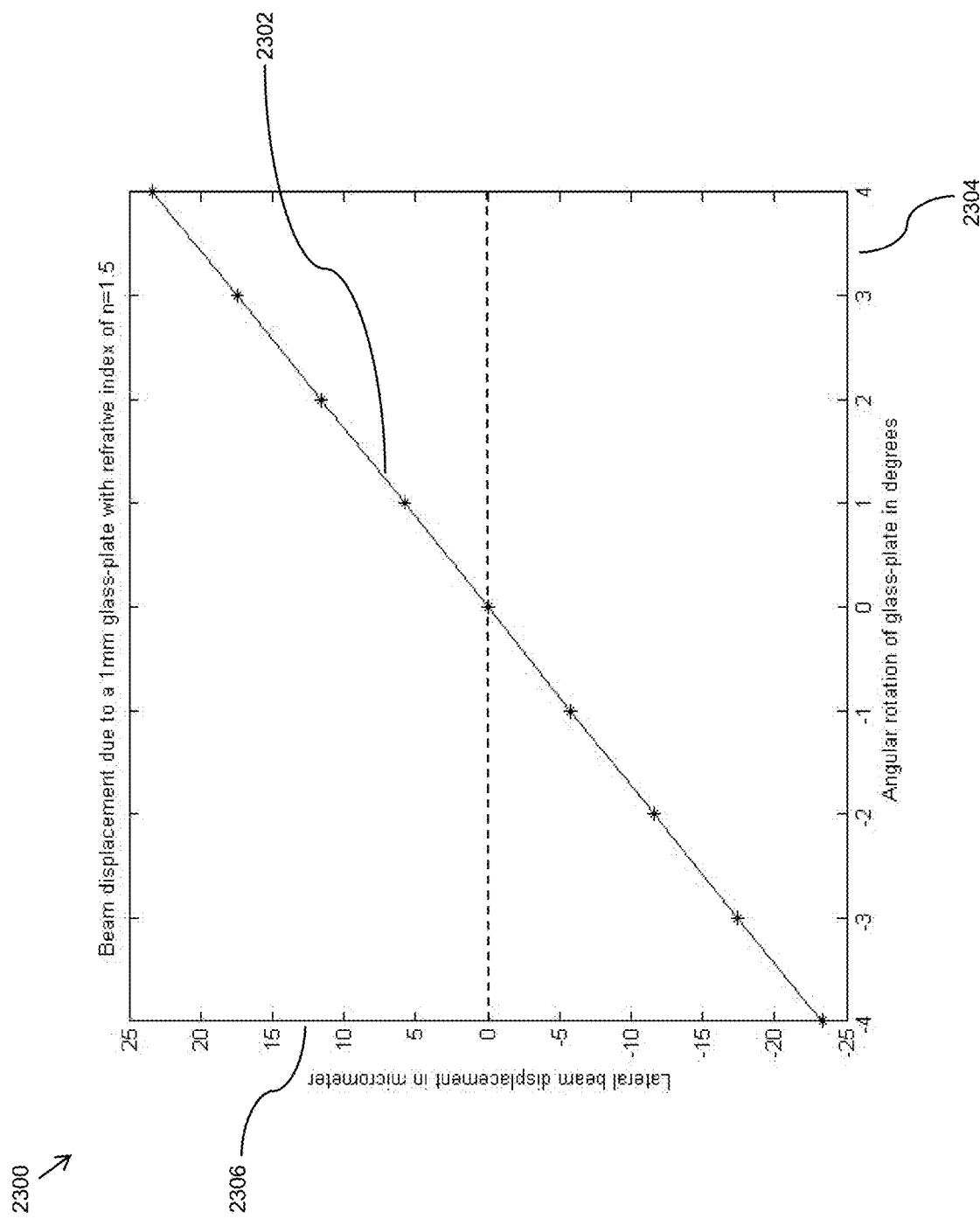
FIG. 23 illustrates lateral image displacement ranges that can be achieved with a single glass slab that can be positioned at various angles with respect to the imager.

FIG. 23 illustrates lateral image displacement ranges that can be achieved with a single glass slab that can be positioned at various angles with respect to the imager. In FIG. 23, the magnitude of lateral image shift 2306 that can be achieved out of a 1 mm thick glass-plate for various angular rotations 2304 compared to the horizontal case (flat-glass plate is parallel to the image sensor and the lens plane) are shown. The glass-plate may be placed on two PZT elements that are driven in synch to cause small tilt of the plate. As seen in the depicted curve 2302, for one degree rotation in either direction (+ or −), the lateral shift can be 5 micrometers. Current imaging sensors have pixel sizes in that range. Of course, by reducing the plate thickness, or the rotation angle, the shift can be reduced as needed. The plate may only have three positions (+angle, −angle and zero) and an image is taken at each position.

Figure 24A:
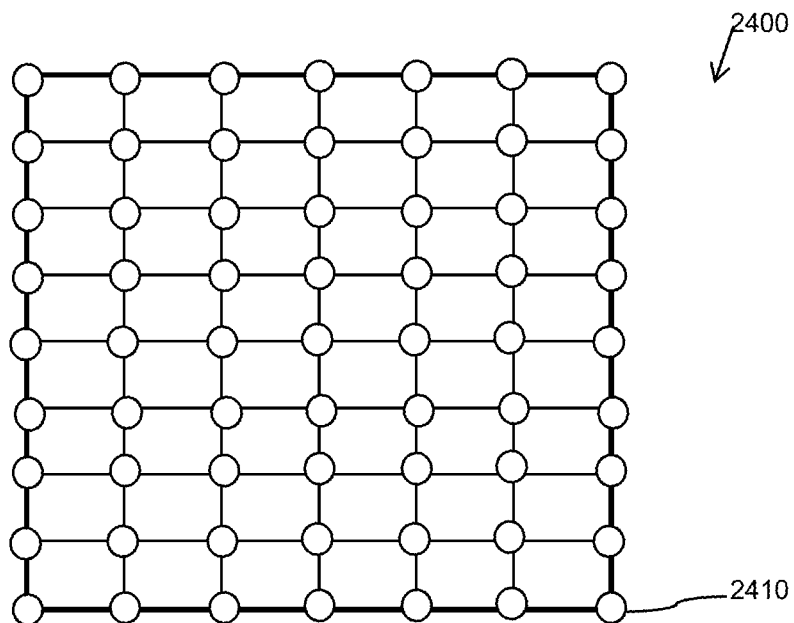
FIG. 24a illustrates image pixels in a standard camera.
Figure 24B:
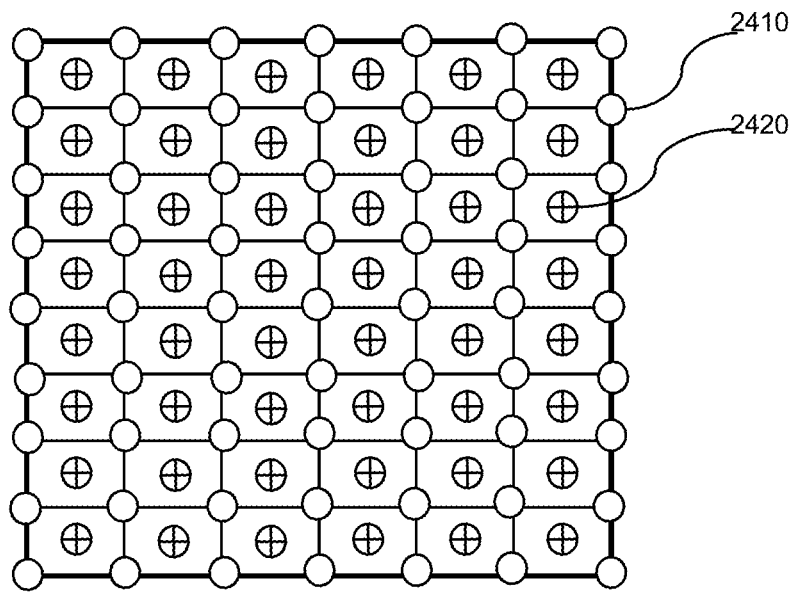
FIG. 24b shows the virtual pixels that are obtained by diagonal displacement of the image across the imager and their locations with respect to the real pixels.

Image data for only a sub-window of the total FOV can be recorded to reduce power consumption. The images are taken after each glass-plate or mirror movement or in a controlled manner. This requires synchronization between movement of the mirror or the glass-plate and image capturing device. The original image and the sub-pixel shifted images (after image registration) are combined through processing to create a higher resolution image. FIG. 24a illustrates image pixels in a standard camera and FIG. 24b shows the virtual pixels that are obtained by diagonal displacement of the image across the imager and their locations with respect to the real pixels. In FIG. 24a, actual image pixels 2410 of a standard camera are shown with open circles while in FIG. 24b the enhanced version of the same image sensor is illustrated. In FIG. 24b, the newly introduced virtual pixels 2420 are shown with a plus sign inside the open circle. As seen in by comparing the two figures, the pixel resolution has been doubled through sub-pixel image shifting.

In MVC design, two scene camera modules are used—one on each side of the eyeglasses frame. One camera will be standard (has no vibrating element) and the other one has a vibrating mirror or plate. Depending on a particular application, the two cameras can have similar or dissimilar lenses and imagers.

In one embodiment, two cameras that have identical lenses and imagers are deployed. While one camera takes normal pictures, the other camera (sub-pixel shift) takes pictures with any sub-pixel accuracy. Videos from the normal camera can be broadcast or shared with no additional processing. However, the second video has to be processed to produce a higher resolution video. This additional processing step may be done on the mobile device (at a higher computing cost) or may be done on a server during live broadcast, or when the video is downloaded to a PC. As in the first approach, not all the pixel values are to be recorded when the objective is to follow the gaze-point of a user.

It should be noted that standard SR techniques require extensive computations and most of this computation is used to register the various low resolution images properly before constructing a high resolution image. The significance of our proposed techniques is that the image shift across the sensor array is controlled precisely and consequently, all the recorded frames are already registered.

In terms of super-resolution practicality, a number of researchers have already implemented SR on FPGA platforms [25-29]. Various resolution enhancement algorithms described in this application are simpler than those that have already been implemented in FPGA. To preserve battery life, the resolution enhancement step may be done as a post-processing step, or be done in real-time on a remote server.

Additional Implementations

One approach in image super resolution is called learning-based or patch-based super resolution [5, 28-30]. In this approach, a database of images that have common features or shapes are used as auxiliary tools. A related area is enhancing a video of a static scene via HR photographs [29]. In our case, the HR camera takes a HR image of the scene at the same time as the LR image is taken. This means that MVC does not need to form a database or search for patterns in it. From a different viewpoint, the images of the HR camera form a relevant temporal database for image enhancement. This means that the existing pattern-based image enhancement techniques can be easily applied to the HR and LR images.

Human eyes cannot see well in the dark but there are cameras (IR or night vision) that can be used for imaging in dark conditions. In another embodiment, a two-mode camera is used to enable recording during day and night. One camera is normal and it records in daylight conditions, and the other camera has infra-red detectors to record in dark conditions. Infra-red detectors of many types may be used. For minimal improvement, existing CMOS detectors are used in conjunction with an optical filter that allows only the IR light to get in and blocks white light (blue, green and red). Other IR detectors have much better quantum efficiencies at IR than CMOS detectors. By using such detectors, better night images are obtained. In one embodiment, one side of the eyeglasses frame has day vision and the other has night vision.

In still another embodiment, additional cameras are placed on the side of the temples of the eyeglasses frame to achieve a total FOV around 270 degrees which is much larger than what human eyes can achieve. These additional cameras are always looking sideways. This is useful for virtual reality applications or for interactive revisit of a scene or an experience.

It is possible to separate the optical lenses from the imaging detector by employing a length of fiber imaging devices such as those manufactured by Schott. Such fiber currently can achieve a resolution of 50 LP/mm. An advantage of using this scheme is to consume much less or no electrical power in the frame area. In another embodiment, the eyeglasses are made totally passive by using such imaging fibers to monitor the user's eye for eye tracking purposes. Using an imaging fiber to couple the light from a lens to a detector is applicable to various embodiments.

Existing image sensors have a fixed aspect ratio of 4:3 for Standard Definition TV and 16:9 for High Definition TV. In the case of MVC, a larger FOV is needed to select a subset of the FOV for SDTV or HDTV video. The optimum aspect ratio for MVC application is 1:1 which means the detecting area is square.

In various embodiments, the resolution enhancement processing described herein may by performed by the image cameras, on a computer on a network after the images are transmitted to the computer over the network, or on a personal computer after video images are downloaded from the MVC to the personal computer. In still other embodiments, the high resolution video capturing device is embedded in a wearable device and the cameras are embedded within the frame of eyeglasses.

In various embodiments, the MVC allows a user the following options to record the video: a) only what the user saw; b) only the scenes that the user did not pay attention to; or c) record the videos from all scene cameras and have the option to view what was seen or was not seen.

In still other embodiments, the eye tracking signal for scene selection is provided by a second person who is wearing a similar eye tracking device as the user of the MVC and uses his/her eye movement to select a scene within the FOV of the first user.

In still other embodiments, the MVC cameras use a circular buffer to continuously record video. As soon as the user decides to save what is in the said buffer, the camera system will continue recording and the buffered video becomes the beginning part of the recorded clip.

Personal Search Engine

Given the ease of use of a hands-free video recording device as discussed herein, each user may generate a huge amount of recorded personal video each year. Therefore, it is very important to be able to index, search, sort, and retrieve the recorded information to make the MVC a more useful device. To do this, personal search engine software that is configured to crawl through the videos and indexes them as soon as they are downloaded to a server or a PC with proper software may be used in a at least one embodiment. For example, the personal search engine software may employ voice to text technology and Query by Humming (QbH) to create keywords based on the audio information part of the video. Also shape and face recognition are used to further index the videos. MPEG-4 and MPEG-7 standards make it possible to search for objects in video images. In various embodiments, the search engine indexes the recorded video based on metadata from any of the physical or physiological sensors of MVC. In a particular embodiment, QbH is used to index the audio portion of the video. In other embodiments, Voice-to-Text or Face Recognition is used to for indexing the data. In still another embodiment, MPEG-7 is used to index objects in the video. In some embodiments, the data and the search engine reside on a server to which the MVC has access through wireless networks or any other communication network.

The search engine can be trained by associating names to faces and this can be further used to index personal videos or used as a real time tool for people who forget names and need them instantly (memory patients are usually embarrassed to acknowledge their limitations to people that they meet). The search engine is also capable of summarizing a video and in doing so individuals can create daily summaries of their lives or compile their own life stories by editing the summaries. The daily summaries can also be posted as video logs (vlogs) online. In a at least one embodiment, the personal search engine software resides on a network server which receives recorded information, such as video and audio, from the mind-view video recorder and stores it within one or more network storage devices. The personal search engine software then indexes the recorded information and makes it searchable for future access by the user of the device or for sharing with others. In a particular embodiment, the mind-view video recorder communicates with the server via one or more wireless networks.

Video summaries can be created in different ways. One criterion for summarizing videos is based on the recorded brainwaves. Each segment summary may be chosen based on the intensity of the brainwaves. Parts of the video segment where attention is reduced may be ignored and the total length of the summary could be subject to a time constraint. Another criterion for summarization could be location change. As previously discussed, the MVC may employ a GPS or utilize wireless signals to extract the location information and use it as a tag or metadata.

Applications of MVC in Healthcare

MVC as a Memory Aid

MVC records not only video and audio, but it has a number of sensors that keep track of temperature and location. In some embodiments, the MVC may function as a memory aid used by people suffering from memory disorders such as dementia and in particular Alzheimer's. The captured information constitutes at least 90% of "short-term memory" information. With the use of the personal search engine, a user can search and retrieve information or reply some experiences to reinforce user's memory. Additionally, by utilizing face identification and object recognition, a person with cognitive impairments can recognize friends and family members. The tool may display the name, say it aloud or whisper in the user's ears. At times a memory patient may misplace an object in an unusual place. The caregivers can use the tool to locate the object.

MVC for Tele-Medicine

One of the difficulties that telemedicine faces is the lack of high quality and yet flexible video stream that could match the capabilities of a physician's eyes. At a doctor's office, a doctor can at will turn his head and eyes in any direction for examination. For telemedicine application, MVC will let the cameras follow user's eyes when the user is describing the situation and symptoms to the doctor. The doctor may want to examine certain areas within the field of view of the patient closely. For this case and with patient's permission, MVC will allow the doctor to control the cameras via the doctor's eyes. Of course in this case, the doctor needs to wear his/her own pair of MVC programmed for doctors or move a mouse on the region of interest to get obtain higher resolution images from that area.

MVC as a Diagnostics Tool

Eye tracking has been used to diagnose children with attention deficit. Doctors can use MVC to study effects of medications on such children. By wearing the device before and after medications or long term treatments, doctors can get a measurable indication of efficacy of the medicine or treatment.

MVC as Feedback Tool for Deep Brain Stimulation and Other Similar Devices

There are a number of diseases such as Essential Tremor, Multiple Sclerosis and Parkinson's that lead to involuntary hands movements or shacking. In extreme cases, a technique such as Deep Brain Stimulation is used. In this approach, tiny electrodes are implanted in the brain. The amplitude and frequency of signals are adjusted by a health professional to minimize the shacking. However, it turn out that patients require repeated re-adjustment of the device as their conditions change. This requires a visit to a doctor or a hospital, which is not convenient. Given the shaking frequency is a few Hertz, MVC can accurately measure the frequency and magnitude of the shakes. This information can in return be used as feedback for the device to dynamically adjust itself.

MVC as Hands-Free Camcorder and Interface Device for People with Disabilities

Video recording application of MVC is obvious. In addition to video recording, they could also use the eye tracking interface to do other tasks such to control a wheelchair, or turn on and off a TV or another device.

MVC for Relapse Prevention

In particular embodiments, the MVC may be used for real-time monitoring of subjects such as to achieve behavioral change in a subject. Relapse is a process and not an instant event. Individuals that go through rehabilitations need proper follow up monitoring to avoid relapses. Through MVC, face and pattern recognition and the search engine, individuals can be warned to stay away a select group of others and places. The individuals can also be randomly monitored for adherence to the program guidelines.

MVC for Patient-Care

Patients and nurses can benefit from using MVC. A nurse can document how he/she treated a patient and when and what medications were used. This is especially true in case of terminally ill people whose relatives cannot be with them all the time to monitor their loved ones as they receive care.

MVC as a Tool for Clinical Trials

Clinical trials are very expensive and time consuming procedures. Participants are required to record or communicate their conditions, side-effects or etc. Many times, people delay taking such note because it is not convenient or possible. In the process, people may forget totally or provide an estimate at a later time. In case of complications, clinical trial organizers can review the chain of events to better identify the cause of adverse effects.

MVC as a Hands-Free Camcorder for People Who Cannot Use their Hands

People with essential tremor cannot use the existing hand-held video recorders because their hands shake involuntarily as they want to use their hands. This results in blurry images and videos which are hard to watch. With MVC, anyone who cannot use their hands, for any reason, could use their eyes to record a high quality video of the scenes of interest.

MVC for Dentist and Hygienists

By wearing an MVC, such professionals can share what they see (as they perform a procedure) with their patients by displaying what they see on a TV monitor that is usually in the room.

Applications of MVC in Media and Entertainment

MVC for Social Networking

In case of Twitter, users exchange short text messages with each other. With MVC connected to a wireless network directly or using connection of a smart-phone, users can share their visual experiences in real-time or may post them online for friends and "followers" to view.

MVC for Extreme Sports

Currently, athletes are seen through TV cameras. With MVC, additional angles are recorded from the athletes' perspective.

MVC to Capture Unexpected Moments

Everyone has un-expected moments that wish could have been captured. A road accident, a child's first step, a burglary in action and many other unexpected moments can be captured with MVC. This is done through continuous recording to MVC's circular buffer.

MVC as a Tool for Citizen Reporters

Citizen reporters with MVC can be their own cameraperson and reporter. This reduces their cost.

MVC as a Tool for Real Estate Agents

Real estate agents can use MVC to send an overview of a new property that they have been informed of to a prospective buyer. Many times, buyers need particular information that is not included in a virtual tour or in the advertisement sheet of the house. There are also houses that have no virtual tour. An agent who has an MVC can capture the information and send it to house hunters. House hunters can also benefit from MVC. After seeing more than a few houses, people start to confuse one house for another. In such cases, a visual record of what was seen can save the times of the agents and house hunters by eliminating the need for multiple visits.

MVC as a Tool for Tele-Presence

For a true tele-presence experience, two camera views are needed: one camera will look at the user and his/her surrounding, and the other camera captures what the user sees. A video conferencing camera functions as the camera and MVC as the second.

MVC for Making Documentaries and Movies

MVC allows a director to shoot a scene exactly how he/she wants by using his own eyes. Actors and Actresses can also record a scene from their own viewpoints. Such video clips can be edited to make a movie.

MVC as a Tool for Referees for Instant Replies or to Share What they Saw

TV camcorders cannot cover all angles. It will be nice to show spectators what a referee saw before he/she made a call.

MVC as a Camcorder for Animals and Pets

MVC optimized for pets and animals will allow a user to see what they pay attention to.

Applications of MVC in Education

MVC as a Tool for Preparing do it Yourself Instructions

Many products require do-it-yourself assembly. However, the written instructions are hard to follow for many people. Preparing a professional video of instructions is costly too. However, the manufacturer can use an MVC to show how the product is assembled step by step.

MVC as a Teaching Tool at Schools

Children have different reading abilities. As a child starts to read a new book, there are words that he/she does not know how to pronounce or their meaning. MVC can be an always available resource to school children. From the analysis of eye movements, it is possible to predict if the reader needs help. MVC can also work as an interface by interpreting hand gestures. For example, a finger pointed at a word may signify more information about the word. From a dictionary database pronunciations or meanings can be provided. The user may also "cut and paste" a sentence or a paragraph from the book via finger gestures. In the same manner as reading application, MVC can be used for math education.

MVC as a Feedback Tool for Coaches

Many times players do not perform a task as a coach directs. For example, a swimming coach may suggest a particular stroke technique. Capturing and replaying a performance immediately is an invaluable teaching tool.

MVC as an Interface Device Between Man and Machine

When using computers, occasionally there is a need to move the cursor to a new location on the screen. In some embodiments, the eye tracking eye-wear is used as an interface device between man an machine. Instead of grabbing the mouse and moving it to the new location, eye or hand movements can be used to keep the curser close or at the gaze-point.

In a particular embodiment, the machine is a tunable lens for vision accommodation. In still other embodiments, the machine may be a personal computer, a mobile phone, a home appliance such as a television set, an automobile, an electronic book, binoculars, or a wheelchair.

MVC as a Feedback Tool and Quality Control for People Working on Assembly Line

When people are observed from close proximity, they may become nervous. There are also times needs to transfer "to-do-it-yourself" instructions accurately. In both cases, MVC can be used to monitor someone or communicate how a skilled person performs a task. A supervisor sitting in an office can randomly check various stations remotely.

MVC as a Fast Documentation Tool

With MVC one can record visual information at ease while adding commentary. After severe traffic accidents, a detailed report needs to be prepared with pictures and information about locations of various objects in the scene. These are time consuming activities and result in keeping roads closed for longer periods of time. MVC can record what an officer sees and use pattern recognition and triangulation to measure and report various objects and their locations. Also police officers who stop a car or search a property can document their search and findings.

MVC as a Time Management Tool

MVC equipped with pattern recognition and personal search engine can be used to provide feedback on how a user spends his/her time. For example, 3 hours in front of TV, 10 visits to refrigerator, 2 hours in front of computer, 90 minutes driving and etc.

MVC for Weight Control

Many weight loss control programs suggest participants to keep a daily log of what they eat. This is a difficult task for most people on those programs. With MVC and its search engine, an accurate record of what people eat, how many times they eat and etc can be complied. Such records can be used by weight loss counselors to propose proper corrective actions.

Applications of MVC in Safety and Security

MVC for Identifying Missing or Wanted People

MVC follows user's eyes and has wireless access to transmit its images to a remote site or server. A security officer equipped with MVC can walk in a public place such as a mall or in an airport while looking at various faces. Images of faces are taken and transferred to a remote server for possible match with wanted individuals who might be missing people or wanted criminals. Face recognition can be done in seconds and if a match is found, the officer can be informed to take proper action.

MVC for Personal Safety and Security

Lone individuals concerned about their personal safety can choose to be monitored live by a relative, friend or a security service for any duration of time.

MVC for Command and Control Training

Many times trainees go through staged training to learn a task or to show mastery of the required skills. To provide effective feedback to such participants, knowledge of what they saw and what they missed is crucial. MVC provides an exact copy of what they saw and what they did not pay attention to. Hence, this video can be used for fact-based training feedback.

MVC as a Wearable Speed Detector

In particular embodiments, the MVC is used as a visual detector to measure speed of cars. In such embodiments, the MVC can record in 3D. Stereo imaging can be used to estimate the distance of one or many objects from the cameras, for example through triangulation techniques. Existing radar detectors that police officers use are heavy and have to be aimed accurately at a car to measure its speed. Via the MVC's stereo imaging, a car's speed can be measured and the recorded video can also be used as unbiased evidence. In at least one embodiment, eye tracking data from eye tracking data from cameras are used to calculate the distance of the wearer of the MVC from a point of interest.

MVC for Multi-Operator Tasks

In hazardous environments, the amount of time that an operator may spend may be limited due to health risks. In such situation, the next operator can watch through the current one to know what exactly has been done before he/she continues the work. The same thing can be achieved in a medical emergency. A doctor at a hospital can watch through a paramedic's eyes to understand the situation better and prepare for the patient's arrival.

MVC for Compliance by Court Orders

Many times individuals are required by law to stay away from certain acts, places or individuals. For example, pedophiles must abstain from certain activities while they are on parole. A remote monitoring station can simultaneously check on such individuals activities provided they are wearing their MVC. An eye recognition program can ensure MVC is worn by the right individual.

MVC as a Tool to Broadcast Traffic Conditions or Accidents by Drivers

Drivers can use MVC to broadcast road condition or report details of an accident to traffic or accident centers.

MVC as a Tool for Teenagers and Elderly Drivers

MVC will see and understand the road signs such as speed limits, stop signs and traffic lights. It has its own speedometer (from how fast objects move in a 3D scene). Once worn, it could warn the drivers about approaching a red light, a stop sign, green light turning yellow, speed limit on the road, getting out of your lane and etc. It is possible that teenagers will be required by the law to wear this device after one offense. For elder drivers with low-vision, MVC could be a driving aid tool.

MVC for Remote Assistance and Collaborations

In particular embodiments, the MVC is provided with direct wireless access to facilitate real-time collaborations. Through the MVC, one can see through someone else's eyes. This makes the MVC a good tele-presence tool for remote assistance. For example, one can help someone else to do a task as if watching over the person's shoulder. In particular embodiments, the real-time collaboration is for field service and troubleshooting. In still other embodiments, the real-time collaboration is used for command and control for public safety and security. In other embodiments the real-time collaboration is used to enable tele-diagnostics or complement video conferencing for tele-presence.

MVC in Emergencies

People panic when an emergency arises. Some can't talk but their eyes can still see. By live broadcasting of what a user sees (or being activated by 911), help and rescue teams can learn much more about the case and become better prepared to take proper actions.

There are other emergencies that MVC can be used to coordinate efforts or provide more info to all involved. For example, when police needs to enter a house, the officers in the front line can use MVC to show what they see to the support officers. Similar information exchange can happen at a fire scene where multiple firefighters view the scene from different angles. An operation command center can watch all the feeds simultaneously to decide on the best course of action. An officer stopping a driver can immediately take a video clip of his/her interaction. There have been cases where a police officer is shot dead when stopping a driver or running into other such encounters.

MVC in a Battle-Zone

Soldiers can share what they see in the front line with the support team. Alternatively, the support team may advise the soldiers on the situation. A remote doctor may guide a soldier to provide help for self or others.

MVC as a Tool in Public Safety

In case of an accident, responders come at different times. Through MVC and its live broadcast capabilities, the first responder can provide live video of the scene while at the same he/she is focusing on his/her own duties. Those who survey the accident scene can also use MVC to document locations of various objects on the scene.

It will be appreciated by those skilled in the art having the benefit of this disclosure that this METHOD AND APPARATUS FOR A COMPACT AND HIGH RESOLUTION MIND-VIEW COMMUNICATOR provides a video recorded that is integrated with eyeglasses to record a scene that is being viewed by a user. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

APPENDIX I

References

[1] "A Novel Method of Video-Based Pupil Tracking", Proceedings of the 2009 IEEE International Conference on Systems, Man and Cybernetics, San Antonio, Tex., USA—pp. 1255-1262, October 2009

[2] D. Li, D. Winfield and D. Parkhurst, "Starburst: A Hybrid algorithm for video based eye tracking combining feature-based and model-based approaches", Iowa State University, Ames, Iowa

[3] "A High Speed Eye Tracking System with Robust Pupil Center Estimation Algorithm", Proceedings of the 29th Annual International Conference of the IEEE EMBS, Kyon, France, pp. 3331-3334, August 2007

[4] P. Milanfar, *Super-Resolution Imaging*, CRC Press (2011)

[5] S. Chaudhuri, *Super-Resolution Imaging*, Kluwer Academic Publishers (2001)

[6] V. Bannore, *Iterative-Interpolation Super-Resolution Image Reconstruction*, Springer (2009)

[7] B. K. Gunturk, "Super-resolution imaging", in *Computational Photography Methods and Applications*, by R. Lukac, CRC Press, 2010

[8] J. Goodman, *Introduction to Fourier Optics*, $2^{nd}$ edition, 160-165, McGraw-Hill, 1988

[9] R. W. Gerchberg, "Super-resolution through energy reduction", Optica Acta, Vol. 21, No. 9, pp. 709-720, (1974)

[10] A. Papoulis, "A new algorithm in spectral analysis and band-limited extrapolation", IEEE Transactions on Circuits and Systems, Vol. 22, No. 9, pp. 735-742, (1975)

[11] E. Gur and Z. Zalevsky, "Single-image digital super-resolution a revised Gerchberg-Papoulis algorithm", Internation Journal of Computer Science, 34:2 (2007)

[12] D. Keren, S. Peleg, R. Brada, "Image sequence enhancement using sub-pixel displacements", Proceeding of IEEE Computer Society Conference on Computer Vision and Pattern Recognition (CVPR '88), pp. 742-746, (1988)

[13] J. Bardsley, S. Jefferies, J. Nagy, and R. Plemmons, "Blind iterative restoration of images with spatially-varying blur", Optics Express, pp. 1767-1782, (2006)

[14] T. R. Lauer, "Deconvolution with spatially-varying PSF", Optics Express, pp. 1767-1782, (2006)

[15] P. C. Hansen, J. G. Nagy, D. P. O'Leary, *Deblurring Images: matrices, Spectra and Filtering*, SIAM (2006)

[16] S. H. Lim, A. Silverstein "Estimation and removal of motion blur by capturing two images with different exposures", HP Laboratories, www.hpl.hp.com/techreports/2008/HPL-2008-170.pdf, (2008)

[17] S.-W Jung and S.-J. Ko, "Image deblurring using multi-exposed images" in *Computational Photography Methods and Applications*, by R. Lukac, CRC Press, 2010.

[18] K. Kubala, E. R. Dowski, and W. T. Cathey, "Reducing complexity in computational imaging systems," Opt-Express 11, 2102-2108 (2003)

[19] E. R. Dowski, and W. T. Cathey, "Extended depth of field through wavefront coding," Applied Optics 34, 1859-1866 (1995)

[20] W. T. Cathey, E. R. Dowski, "New paradigm for imaging systems," Applied Optics 41, 6080-6092 (2002)

[21] S.-H. Lee, N.-C. Park, and Y.-P. Park, "Breaking diffraction limit of a small f-number compact camera using wavefront coding," Optics Express 16, 13569-13578 (2008)

[22] L. G. Brown, "A survey of image registration techniques", J. ACM Computing Surveys, Vol 24, 4 Dec. 1992

[23] B. Zitova, J. Flusser, "Image registration methods: a survey", Image and Vision Computing, 997-1000, 21 (2003)

[24] P. Vandewalle, S. Susstrunk, and M. Vetterli, "A frequency domain approach to registration of aliased images with applications to super-resolution", EURASIP Journal on Applied Signal Processing, pp. 1-14, (2006)

[25] M. E. Angelopoulou, C.-S. Bouganis, P. YK. Cheung, and G. A. Constantinides, "FPGA-based real-time super-resolution on an adaptive image sensor", Proc. Applied Reconfigurable Computing 2008, pp. 125-136 (2008)

[26] Maria Angelopoulou, Christos-Savvas Bouganis, Peter Y. K. Cheung, and George A. Constantinides "Robust Real-Time Super-Resolution on FPGA and an Application to Video Enhancement", ACM Transactions on Reconfigurable Technology and Systems (2009)

[27] O. Bowen, C-S Bougani, "Real-time image super-resolution using an FPGA", Field Programmable Logic and Applications, (2008)

[28] W. T. Freeman, T. R. Jones, and E. C. Pasztor, "Example-based super-resolution", IEEE Computer Graphics and Applications, pp. 56-65 (2002)

[29] P. Bhat, L. Zitnick, N. Snavely, A. Agarwala, M. Agrawala, B. Curless, M. Cohen, S. Kang, "Using photographs to enhance videos of a static scene", Eurographics Symposium on Rendering (EGSR) (2007)

[30] U.S. Pat. No. 7,715,658 B2, May 11, 2010 Apparatus and Method for Super-Resolution Enhancement Processing.

What is claimed is:

1. An imaging method for a multi-camera device, comprising:
   capturing a first image of a scene with a first camera, the first camera having a first field of view, and the first image having a first image resolution,
   capturing a second image with a second camera, the second camera having a second field of view, and the second image having a second image resolution, wherein the second image resolution is higher than the first image resolution and the second field of view is smaller than the first field of view, and wherein the second image corresponding to a subset of the scene that is within the first field of view, receiving the first image and the second image by at least one processor, the at least one processor configured for:
    registering a subset of the first image to a subset of the second image,
    calculating, based on at least one of the first image and the second image, the distance of at least one object in the scene from the multi-camera device,
    generating, based at least upon the calculated distance of the at least one object in the scene from the multi-camera device and at least one of the received images, an output image corresponding to a portion of the scene that is within the field of view of the first camera, wherein the output image having at least two image regions, an inner image region and an outer image region, the outer image region surrounding at least partially the inner image region, and at least a subset of the inner image region includes a portion of the at least one object, wherein the image resolution of the inner image region is higher than the image resolution of the first image and the image resolution of the outer image region is lower than the image resolution of the first image, and saving the output image,
    whereby the inner image region of the output image appears to a human eye as sharp and clear and the outer image region of the output image appears to the human eye as relatively blurry.

2. The imaging method of claim 1 further including reducing the resolution of at least a subset of one of the received images via an image processing technique.

3. The imaging method of claim 1 wherein the first and the second cameras are color cameras and generate color images.

4. The imaging method of claim 1 wherein the image resolution of the inner image region of the output image is the same as the second image resolution.

5. The imaging method of claim 1 wherein the output image corresponding to the subset of the scene that is within the second field of view.

6. The imaging method of claim 1 further including monitoring a movement of at least one of the cameras via at least one accelerometer.

7. The imaging method of claim 1 further including capturing the location information of the multi-camera device via a GPS.

8. An imaging apparatus comprising:
    a first camera having a first field of view for capturing a first image of a scene, wherein the first image having a first image resolution,
    a second camera having a second field of view for capturing a second image, wherein the second image having a second image resolution and the second image resolution is higher than the first image resolution and the second field of view is smaller than the first field of view, and wherein the second image corresponding to a subset of the scene that is within the field of view of the first camera,
    at least one processor, in communication with the first camera and the second camera, the at least one processor configured for:
        receiving the first image and the second image,
        registering at least a subset of the first image to a subset of the second image,
        calculating, based on at least one of the first image and the second image, the distance of at least one object in the scene from the imaging apparatus,
        generating, based at least upon the calculated distance of the at least one object in the scene from the imaging apparatus, an output image corresponding to a portion of the scene that is within the field of view of the first camera, wherein the output image having at least two image regions, an inner image region and an outer image region, the inner image region surrounded at least partially by the outer image region, wherein the image resolution of the inner image region is higher than the image resolution of the first image and the image resolution of the outer image region is lower than the image resolution of the first image, and
        saving the output image,
        whereby the inner image region of the output image appears to a human eye as sharp and clear and the outer image region of the output image appears to the human eye as relatively blurry.

9. The imaging apparatus of claim 8 wherein the first camera is a color camera and includes a color filter array.

10. The imaging apparatus of claim 8 wherein the first image and the second image have the same number of pixels.

11. The imaging apparatus of claim 8 wherein the second camera has a color filter array to generate color images.

12. The imaging apparatus of claim 8 wherein the second camera and the first camera have two different types of color filter arrays.

13. The imaging apparatus of claim 8 wherein the at least one processer is further configured for reducing the image resolution of at least a portion of one of the received images.

14. The imaging apparatus of claim 8 further including a GPS for receiving the location of the imaging apparatus and communicating the location information to the at least one processor.

15. The imaging apparatus of claim 8 wherein the imaging apparatus is disposed on an eyeglass frame.

16. The imaging apparatus of claim 8 wherein the at least one processor further configured for initiating an image projection procedure.

17. The imaging apparatus of claim 8 further including at least one accelerometer to monitor a movement of at least one of the cameras.

18. The imaging apparatus of claim 8 further including at least one microphone for converting an audio signal into an electrical signal.

19. The imaging apparatus of claim 8 further including at least one speaker for converting an electrical signal into an audio signal.

20. An imaging apparatus comprising:
    a first camera having a first field of view and a first color filter array for capturing a first image of a scene, wherein the first image having a first image resolution,
    a second camera having a second field of view and a second color filter array for capturing a second image, wherein the second image having a second image resolution and the second image resolution is higher than the first image resolution, and wherein the second image corresponding to a subset of the scene that is within the field of view of the first camera,
    at least one processor, in communication with the first camera and the second camera, the at least one processor configured to:
        receive the first image and the second image,
        register at least a subset of the first image to a subset of the second image, execute an object recognition procedure to detect an object in at least one of the received images, calculate, based at least on one of the first scene image and the second scene image, the distance of the detected object from the imaging apparatus, generate, based on the calculated distance of the detected object from the imaging apparatus and the at least one of the received images, an output image corresponding to a portion of the scene that is within the field of view of the first camera, wherein the output image has at least two image regions, an inner image region and an outer image region, the inner image region surrounded at least partially by the outer image region, wherein the image resolution of the inner image region is higher than the image resolution of the first image and the image resolution of the outer image region is lower than the image resolution of the first image, and, save the output scene image, whereby the inner image region of the output image appears to a human eye as sharp and clear and the outer image region of the output image appears to the human eye as relatively blurry.

* * * * *